(12) United States Patent
Yang et al.

(10) Patent No.: US 12,419,703 B2
(45) Date of Patent: Sep. 23, 2025

(54) ROBOTIC DRIVE SYSTEM FOR ACHIEVING SUPRA-AORTIC ACCESS

(71) Applicant: Imperative Care, Inc., Campbell, CA (US)

(72) Inventors: Yi Yang, San Francisco, CA (US); Craig Mar, Fremont, CA (US); Michael Luna, San Jose, CA (US); Lilip Lau, Los Altos, CA (US)

(73) Assignee: Imperative Care, Inc., Campbell, CA (US)

( * ) Notice: Subject to any disclaimer, the term of this patent is extended or adjusted under 35 U.S.C. 154(b) by 422 days.

(21) Appl. No.: 17/959,894

(22) Filed: Oct. 4, 2022

(65) Prior Publication Data

US 2024/0033016 A1     Feb. 1, 2024

Related U.S. Application Data

(63) Continuation-in-part of application No. 17/816,669, filed on Aug. 1, 2022.

(51) Int. Cl.
*A61M 25/09*     (2006.01)
*A61B 34/30*     (2016.01)
(Continued)

(52) U.S. Cl.
CPC ......... *A61B 34/30* (2016.02); *A61M 25/0097* (2013.01); *A61M 25/0113* (2013.01); *A61M 25/0127* (2013.01); *A61M 25/09041* (2013.01); *A61B 2034/301* (2016.02); *A61B 2034/303* (2016.02); *A61B 2034/732* (2016.02); *A61M 2039/0258* (2013.01)

(58) Field of Classification Search
CPC ... A61B 34/30; A61B 34/73; A61B 2034/301; A61B 2034/731; A61F 2/95
USPC ......................................................... 604/510
See application file for complete search history.

(56) References Cited

U.S. PATENT DOCUMENTS 1,286,033 A    11/1918   Lambeth
4,819,653 A     4/1989   Marks
(Continued)

FOREIGN PATENT DOCUMENTS

AU     2006268156     4/2012
CN     102462533     5/2012
(Continued)

OTHER PUBLICATIONS

US 12,076,032 B1, 09/2024, Teigen et al. (withdrawn)
(Continued)

*Primary Examiner* — Kira Nguyen
(74) *Attorney, Agent, or Firm* — Knobbe, Martens, Olson & Bear, LLP

(57) ABSTRACT

A drive system for achieving supra-aortic access and neurovascular treatment site access includes a guidewire hub configured to adjust an axial position and a rotational position of a guidewire, a procedure catheter hub configured to adjust an axial position and a rotational position of a procedure catheter, a guide catheter hub configured to adjust an axial position of a guide catheter, and an access catheter hub configured to adjust an axial position and a rotational position of an access catheter, the access catheter further configured to laterally deflect a distal deflection zone of the access catheter.

20 Claims, 28 Drawing Sheets

(51) Int. Cl.
*A61M 25/00* (2006.01)
*A61M 25/01* (2006.01)
*A61B 34/00* (2016.01)
*A61M 39/02* (2006.01)

(56) References Cited

U.S. PATENT DOCUMENTS

| | | | |
|---|---|---|---|
| 4,925,444 A | 5/1990 | Orkin | |
| 5,037,404 A | 8/1991 | Gold et al. | |
| 5,131,391 A | 7/1992 | Sakai et al. | |
| 5,380,268 A | 1/1995 | Wheeler | |
| 5,638,818 A | 6/1997 | Diab et al. | |
| 5,882,333 A | 3/1999 | Schaer et al. | |
| 5,989,208 A | 11/1999 | Nita | |
| 6,096,004 A | 8/2000 | Meglan et al. | |
| 6,375,471 B1 | 4/2002 | Wendlandt et al. | |
| 6,400,971 B1 | 6/2002 | Firanov et al. | |
| 7,192,433 B2 | 3/2007 | Osypka et al. | |
| 7,214,230 B2 | 5/2007 | Brock et al. | |
| 7,331,967 B2 | 2/2008 | Lee et al. | |
| 7,379,790 B2 | 5/2008 | Toth et al. | |
| 7,556,611 B2 | 7/2009 | Kolenbrander et al. | |
| 7,567,233 B2 | 7/2009 | Garibaldi et al. | |
| 7,608,083 B2 | 10/2009 | Lee et al. | |
| 7,615,042 B2 | 11/2009 | Beyar et al. | |
| 7,727,185 B2 | 6/2010 | Weitzner | |
| 7,747,960 B2 | 6/2010 | Garibaldi et al. | |
| 7,756,308 B2 | 7/2010 | Viswanathan | |
| 7,761,133 B2 | 7/2010 | Viswanathan et al. | |
| 7,789,874 B2 | 9/2010 | Yu et al. | |
| D626,250 S | 10/2010 | Wenderow et al. | |
| 7,818,076 B2 | 10/2010 | Viswanathan | |
| 7,831,294 B2 | 11/2010 | Viswanathan | |
| 7,850,640 B2 | 12/2010 | Williams et al. | |
| 7,850,642 B2 | 12/2010 | Moll et al. | |
| 7,853,306 B2 | 12/2010 | Viswanathan et al. | |
| 7,884,727 B2 | 2/2011 | Tran | |
| 7,886,743 B2 | 2/2011 | Cooper et al. | |
| 7,887,549 B2 | 2/2011 | Wenderow et al. | |
| 7,909,798 B2 | 3/2011 | Osypka | |
| 7,951,243 B2 | 5/2011 | Boyle, Jr. et al. | |
| 7,955,316 B2 | 6/2011 | Weitzner et al. | |
| 7,963,288 B2 | 6/2011 | Rosenberg et al. | |
| 8,004,229 B2 | 8/2011 | Nowlin et al. | |
| 8,021,326 B2 | 9/2011 | Moll et al. | |
| RE42,804 E | 10/2011 | Dedig et al. | |
| 8,052,636 B2 | 11/2011 | Moll et al. | |
| 8,083,753 B2 | 12/2011 | Solar et al. | |
| 8,108,069 B2 | 1/2012 | Stahler et al. | |
| 8,114,032 B2 | 2/2012 | Ferry et al. | |
| 8,123,726 B2 | 2/2012 | Searfoss et al. | |
| 8,131,379 B2 | 3/2012 | Hauck | |
| 8,137,317 B2 | 3/2012 | Osypka | |
| 8,146,874 B2 | 4/2012 | Yu | |
| 8,165,684 B2 | 4/2012 | Putz et al. | |
| 8,190,238 B2 | 5/2012 | Moll et al. | |
| 8,220,468 B2 | 7/2012 | Cooper et al. | |
| 8,242,972 B2 | 8/2012 | Garibaldi et al. | |
| 8,244,824 B2 | 8/2012 | Garibaldi et al. | |
| 8,257,302 B2 | 9/2012 | Beyar et al. | |
| 8,262,671 B2 | 9/2012 | Osypka | |
| 8,281,807 B2 | 10/2012 | Trombley et al. | |
| 8,307,693 B2 | 11/2012 | Uram et al. | |
| D674,484 S | 1/2013 | Murphy et al. | |
| 8,343,096 B2 | 1/2013 | Kirschenman et al. | |
| 8,343,098 B2 | 1/2013 | Nystrom et al. | |
| 8,377,077 B2 | 2/2013 | Reis | |
| 8,390,438 B2 | 3/2013 | Olson et al. | |
| 8,399,871 B2 | 3/2013 | Beyar et al. | |
| 8,403,909 B2 | 3/2013 | Spohn et al. | |
| D680,645 S | 4/2013 | Murphy et al. | |
| 8,409,172 B2 | 4/2013 | Moll et al. | |
| 8,467,853 B2 | 6/2013 | Hunter et al. | |
| D685,468 S | 7/2013 | Murphy et al. | |
| 8,480,618 B2 | 7/2013 | Wenderow et al. | |
| 8,498,691 B2 | 7/2013 | Moll et al. | |
| 8,506,555 B2 | 8/2013 | Morales | |
| 8,521,331 B2 | 8/2013 | Itkowitz | |
| 8,529,582 B2 | 9/2013 | Devengenzo et al. | |
| 8,540,698 B2 | 9/2013 | Spohn et al. | |
| 8,551,084 B2 | 10/2013 | Hauck et al. | |
| 8,613,730 B2 | 12/2013 | Hieb et al. | |
| 8,617,102 B2 | 12/2013 | Moll et al. | |
| 8,620,473 B2 | 12/2013 | Diolaiti et al. | |
| 8,671,817 B1 | 3/2014 | Bogusky | |
| 8,672,880 B2 | 3/2014 | Cohen et al. | |
| 8,684,953 B2 | 4/2014 | Cabiri | |
| 8,684,962 B2 | 4/2014 | Kirschenman et al. | |
| 8,694,157 B2 | 4/2014 | Wenderow et al. | |
| 8,740,840 B2 | 6/2014 | Foley et al. | |
| 8,747,358 B2 | 6/2014 | Trombley et al. | |
| 8,790,297 B2 | 7/2014 | Bromander et al. | |
| 8,799,792 B2 | 8/2014 | Garibaldi et al. | |
| 8,800,881 B2 | 8/2014 | Biseta et al. | |
| 8,801,661 B2 | 8/2014 | Moll et al. | |
| 8,806,359 B2 | 8/2014 | Garibaldi et al. | |
| 8,828,021 B2 | 9/2014 | Wenderow et al. | |
| 8,833,293 B2 * | 9/2014 | Horn | F16L 55/1645 |
| | | | 15/104.062 |
| 8,840,628 B2 | 9/2014 | Green et al. | |
| 8,852,162 B2 | 10/2014 | Williams et al. | |
| 8,852,167 B2 | 10/2014 | Trombley et al. | |
| 8,894,610 B2 | 11/2014 | Macnamara et al. | |
| 8,905,969 B2 | 12/2014 | Nystrom et al. | |
| 8,939,963 B2 | 1/2015 | Rogers et al. | |
| 8,961,491 B2 | 2/2015 | Uber et al. | |
| 8,968,333 B2 | 3/2015 | Yu et al. | |
| 8,974,408 B2 | 3/2015 | Wallace et al. | |
| 8,974,420 B2 | 3/2015 | Searfoss et al. | |
| 8,986,246 B2 | 3/2015 | Foley et al. | |
| 9,005,271 B2 * | 4/2015 | Ivancev | A61F 2/07 |
| | | | 623/1.11 |
| 9,056,200 B2 | 6/2015 | Uber et al. | |
| 9,066,740 B2 | 6/2015 | Carlson et al. | |
| 9,070,486 B2 | 6/2015 | Guerrera et al. | |
| 9,095,681 B2 | 8/2015 | Wenderow et al. | |
| 9,101,379 B2 | 8/2015 | Au et al. | |
| 9,111,016 B2 | 8/2015 | Besson et al. | |
| 9,132,949 B2 | 9/2015 | Bideta et al. | |
| 9,138,566 B2 | 9/2015 | Cabiri | |
| 9,168,356 B2 | 10/2015 | Wenderow et al. | |
| 9,186,046 B2 | 11/2015 | Ramamurthy et al. | |
| 9,199,033 B1 | 12/2015 | Cowan et al. | |
| 9,205,227 B2 | 12/2015 | Cohen et al. | |
| 9,220,568 B2 | 12/2015 | Bromander et al. | |
| 9,233,225 B2 | 1/2016 | Hebert | |
| 9,241,768 B2 | 1/2016 | Sandhu et al. | |
| 9,242,252 B2 | 1/2016 | Eberle et al. | |
| 9,259,526 B2 | 2/2016 | Barron et al. | |
| 9,295,527 B2 | 3/2016 | Kirschenman et al. | |
| 9,314,306 B2 | 4/2016 | Yu | |
| 9,314,307 B2 | 4/2016 | Richmond et al. | |
| 9,314,310 B2 | 4/2016 | Kirschenman et al. | |
| 9,314,311 B2 | 4/2016 | Wenderow et al. | |
| 9,314,594 B2 | 4/2016 | Kirschenman | |
| 9,320,479 B2 | 4/2016 | Wenderow et al. | |
| 9,320,573 B2 | 4/2016 | Sandhu et al. | |
| 9,333,324 B2 | 5/2016 | Cohen et al. | |
| 9,345,859 B2 | 5/2016 | Blacker | |
| 9,375,729 B2 | 6/2016 | Eberle et al. | |
| 9,402,977 B2 | 8/2016 | Wenderow et al. | |
| 9,408,669 B2 | 8/2016 | Kokish et al. | |
| 9,427,515 B1 | 8/2016 | Nystrom | |
| 9,427,562 B2 | 8/2016 | Blacker | |
| 9,439,736 B2 | 9/2016 | Olson | |
| 9,447,890 B2 | 9/2016 | Jennings et al. | |
| 9,452,276 B2 | 9/2016 | Duindam et al. | |
| 9,452,277 B2 | 9/2016 | Blacker | |
| 9,474,857 B2 | 10/2016 | Riley et al. | |
| 9,480,797 B1 | 11/2016 | Swantner et al. | |
| 9,488,971 B2 | 11/2016 | Yip et al. | |
| 9,498,291 B2 | 11/2016 | Balaji et al. | |
| 9,510,912 B2 | 12/2016 | Bencteux et al. | |
| 9,517,305 B2 | 12/2016 | Uram et al. | |

(56) References Cited

U.S. PATENT DOCUMENTS

| | | |
|---|---|---|
| 9,532,840 B2 | 1/2017 | Wong et al. |
| 9,533,121 B2 | 1/2017 | Pacheco et al. |
| 9,545,497 B2 | 1/2017 | Wenderow et al. |
| 9,549,783 B2 | 1/2017 | Zirps |
| 9,566,201 B2 | 2/2017 | Yu |
| 9,566,414 B2 | 2/2017 | Wong et al. |
| 9,572,481 B2 | 2/2017 | Duindam et al. |
| 9,585,806 B2 | 3/2017 | Herrig |
| 9,586,029 B2 | 3/2017 | Shekalim et al. |
| 9,603,573 B2 | 3/2017 | Leininger et al. |
| 9,623,209 B2 | 4/2017 | Wenderow et al. |
| 9,629,595 B2 | 4/2017 | Walker et al. |
| 9,636,479 B2 | 5/2017 | Bencteux et al. |
| 9,687,304 B2 | 6/2017 | Bencteux et al. |
| 9,700,698 B2 | 7/2017 | Pacheco et al. |
| 9,707,377 B2 | 7/2017 | Cohen et al. |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,114 B2 | 9/2017 | Murphy et al. |
| 9,770,301 B2 | 9/2017 | Bencteux et al. |
| 9,782,130 B2 | 10/2017 | Hauck et al. |
| 9,782,564 B2 | 10/2017 | Zirps et al. |
| 9,789,285 B1 | 10/2017 | Blacker |
| 9,814,534 B2 | 11/2017 | Wenderow et al. |
| 9,825,455 B2 | 11/2017 | Sandhu et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,101 B2 | 1/2018 | Wenderow et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,993,614 B2 | 6/2018 | Pacheco et al. |
| 9,993,615 B2 | 6/2018 | Blacker |
| 9,999,751 B2 | 6/2018 | Pacheco et al. |
| 10,010,699 B2 | 7/2018 | Cohen et al. |
| 10,029,072 B2 | 7/2018 | Hebert |
| 10,046,140 B2 | 8/2018 | Kokish et al. |
| 10,052,761 B2 | 8/2018 | Langenfeld et al. |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,105,486 B2 | 10/2018 | Trombley et al. |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,178,995 B2 | 1/2019 | Cragg |
| 10,201,314 B2 | 2/2019 | Frederick et al. |
| 10,231,788 B2 | 3/2019 | Olson et al. |
| 10,238,456 B2 | 3/2019 | Murphy et al. |
| 10,245,112 B2 | 4/2019 | Kottenstette et al. |
| 10,258,285 B2 | 4/2019 | Hauck et al. |
| 10,271,910 B2 | 4/2019 | Wenderow et al. |
| 10,299,867 B2 | 5/2019 | Wenderow et al. |
| 10,307,570 B2 | 6/2019 | Blacker |
| 10,322,277 B2 | 6/2019 | Nystrom |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,391,234 B2 | 8/2019 | Sams et al. |
| 10,420,537 B2 | 9/2019 | Salahieh et al. |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,449,007 B2 | 10/2019 | Deboeuf et al. |
| 10,456,556 B2 | 10/2019 | Cabiri |
| 10,512,514 B2 | 12/2019 | Nowlin et al. |
| 10,522,250 B2 | 12/2019 | Spohn et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,583,276 B2 | 3/2020 | Zirps |
| 10,588,656 B2 | 3/2020 | Trosper et al. |
| 10,589,018 B2 | 3/2020 | Uber et al. |
| 10,611,391 B1 | 4/2020 | Klem et al. |
| 10,647,007 B2 | 5/2020 | Cordoba et al. |
| 10,653,863 B1 | 5/2020 | Blacker et al. |
| 10,660,814 B2 | 5/2020 | Soundararajan et al. |
| 10,661,453 B2 | 5/2020 | Koenig et al. |
| 10,687,903 B2 | 6/2020 | Lewis et al. |
| 10,695,140 B2 | 6/2020 | Overmyer et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |
| 10,722,253 B2 | 7/2020 | Deville et al. |
| 10,729,825 B2 | 8/2020 | Boyle, Jr. et al. |
| 10,736,706 B2 | 8/2020 | Scheib |
| 10,737,061 B2 | 8/2020 | Parmar |
| 10,744,302 B2 | 8/2020 | Pacheco et al. |
| 10,765,303 B2 | 9/2020 | Graetzel et al. |
| 10,765,486 B2 | 9/2020 | Bajo et al. |
| 10,779,775 B2 | 9/2020 | Bergman et al. |
| 10,779,895 B2 | 9/2020 | Wenderow et al. |
| 10,783,993 B2 | 9/2020 | Spohn et al. |
| 10,799,305 B2 | 10/2020 | Murphy et al. |
| 10,806,905 B2 | 10/2020 | Asmus |
| 10,813,713 B2 | 10/2020 | Koch et al. |
| 10,814,102 B2 | 10/2020 | Laby et al. |
| 10,820,951 B2 | 11/2020 | Soundararajan et al. |
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafii-Tari et al. |
| 10,835,329 B2 | 11/2020 | Wenderow et al. |
| 10,835,668 B2 | 11/2020 | Novickoff et al. |
| 10,849,702 B2 | 12/2020 | Hsu et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,898,082 B2 | 1/2021 | Sandgaard |
| 10,898,288 B2 | 1/2021 | Dachs, II et al. |
| 10,900,771 B2 | 1/2021 | Kottenstette et al. |
| 10,912,624 B2 | 2/2021 | Prentakis et al. |
| 10,912,924 B2 | 2/2021 | Park et al. |
| 10,945,904 B2 | 3/2021 | de Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,040,147 B2 | 6/2021 | Wagner |
| 11,045,274 B2 | 6/2021 | Dachs, II et al. |
| 11,052,226 B2 | 7/2021 | Salahieh et al. |
| 11,058,508 B2 | 7/2021 | Scheib et al. |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |
| 11,096,712 B2 | 8/2021 | Teigen et al. |

(56) References Cited

U.S. PATENT DOCUMENTS

| | | |
|---|---|---|
| 11,104,012 B2 | 8/2021 | Cordoba et al. |
| 11,109,919 B2 | 9/2021 | Murphy et al. |
| 11,109,920 B2 | 9/2021 | Al-Jadda et al. |
| 11,109,921 B2 | 9/2021 | Kottenstette et al. |
| 11,110,217 B2 | 9/2021 | O'Brien et al. |
| 11,114,918 B2 | 9/2021 | Zirps |
| 11,129,602 B2 | 9/2021 | Wong et al. |
| 11,141,566 B2 | 10/2021 | Cabiri |
| 11,147,950 B2 | 10/2021 | Destrebecq et al. |
| 11,179,213 B2 | 11/2021 | Huang et al. |
| 11,179,546 B2 | 11/2021 | Martin |
| 11,185,455 B2 | 11/2021 | Cagle et al. |
| 11,191,893 B2 | 12/2021 | Capone et al. |
| 11,197,683 B1 | 12/2021 | Teigen et al. |
| 11,207,147 B2 | 12/2021 | Diamond et al. |
| 11,209,300 B2 | 12/2021 | Johnson |
| 11,213,356 B2 | 1/2022 | Tanner et al. |
| 11,213,362 B2 | 1/2022 | Sharon et al. |
| 11,213,654 B2 | 1/2022 | Murphy et al. |
| 11,234,779 B2 | 2/2022 | Fuerst et al. |
| 11,234,781 B2 | 2/2022 | Penny et al. |
| 11,234,784 B2 | 2/2022 | Alden |
| 11,241,291 B2 | 2/2022 | Sharon et al. |
| 11,259,881 B2 | 3/2022 | Garcia Kilroy et al. |
| 11,266,424 B2 | 3/2022 | Hofmann et al. |
| 11,291,515 B2 | 4/2022 | Sharon et al. |
| 11,298,198 B2 | 4/2022 | Fournier et al. |
| 11,304,668 B2 | 4/2022 | Wenderow et al. |
| 11,318,618 B2 | 5/2022 | Desai |
| 11,331,157 B2 | 5/2022 | Russell et al. |
| 11,337,712 B2 | 5/2022 | Teigen et al. |
| 11,337,764 B2 | 5/2022 | Deboeuf et al. |
| 11,357,586 B2 | 6/2022 | Huang et al. |
| 11,357,597 B2 | 6/2022 | Jhaveri et al. |
| 11,359,156 B2 | 6/2022 | Long et al. |
| 11,376,086 B2 | 7/2022 | McGrogan et al. |
| 11,389,360 B2 | 7/2022 | Koenig et al. |
| 11,400,214 B2 | 8/2022 | Porter |
| 11,406,402 B2 | 8/2022 | Deville et al. |
| 11,413,101 B2 | 8/2022 | Sen et al. |
| 11,413,431 B2 | 8/2022 | Blacker |
| 11,419,977 B2 | 8/2022 | Cowan et al. |
| 11,426,246 B2 | 8/2022 | Asadian et al. |
| 11,432,835 B2 | 9/2022 | Shaffer et al. |
| 11,432,840 B2 | 9/2022 | Grothe et al. |
| 11,448,327 B2 | 9/2022 | Heffner et al. |
| 11,464,587 B2 | 10/2022 | Yu et al. |
| 11,464,589 B1 | 10/2022 | Roh et al. |
| 11,472,030 B2 | 10/2022 | Ho et al. |
| 11,478,329 B2 | 10/2022 | Gee et al. |
| 11,490,911 B2 | 11/2022 | Panian |
| 11,497,481 B2 | 11/2022 | Penny et al. |
| 11,497,523 B2 | 11/2022 | Trosper et al. |
| 11,497,568 B2 | 11/2022 | Ho et al. |
| 11,510,736 B2 | 11/2022 | Rafii-Tari et al. |
| D976,399 S | 1/2023 | Carmi |
| 11,547,426 B2 | 1/2023 | Deville et al. |
| 11,547,511 B2 | 1/2023 | Asadian et al. |
| 11,564,649 B2 | 1/2023 | Kedmi-Shahar et al. |
| 11,571,267 B2 | 2/2023 | Gonenc et al. |
| 11,576,743 B2 | 2/2023 | Venkataraman et al. |
| 11,577,382 B2 | 2/2023 | Cagle et al. |
| 11,589,931 B2 | 2/2023 | Desai et al. |
| 11,607,108 B2 | 3/2023 | Yu et al. |
| 11,628,024 B2 | 4/2023 | Kapadia |
| 11,633,247 B2 | 4/2023 | Johnson et al. |
| 11,642,181 B2 | 5/2023 | Nobles et al. |
| 11,653,905 B2 | 5/2023 | Wong et al. |
| 11,660,151 B2 | 5/2023 | Schena |
| 11,660,437 B2 | 5/2023 | Verma |
| 11,672,602 B2 | 6/2023 | Monteverde et al. |
| 11,678,943 B2 | 6/2023 | Zhou et al. |
| 11,678,948 B2 | 6/2023 | Vargas et al. |
| 11,684,759 B2 | 6/2023 | Hayzelden |
| 11,690,985 B2 | 7/2023 | Calhoun et al. |
| 11,696,808 B2 | 7/2023 | Blacker et al. |
| 11,696,810 B2 | 7/2023 | Asadian et al. |
| 11,701,196 B2 | 7/2023 | Scheib et al. |
| 11,703,604 B2 | 7/2023 | Dissertori et al. |
| 11,712,805 B2 | 8/2023 | Zhou et al. |
| 11,713,376 B2 | 8/2023 | Leroux et al. |
| 11,717,356 B2 | 8/2023 | Amiri et al. |
| 11,717,640 B2 | 8/2023 | Fantuzzi et al. |
| 11,723,739 B2 | 8/2023 | Asadian et al. |
| 11,723,744 B2 | 8/2023 | Ergueta Tejerina et al. |
| 11,730,499 B1 | 8/2023 | Thio et al. |
| 11,737,821 B2 | 8/2023 | Algawi et al. |
| 11,744,989 B2 | 9/2023 | Blacker |
| 11,759,269 B2 | 9/2023 | Zhou et al. |
| 11,764,873 B2 | 9/2023 | Burla et al. |
| 11,765,360 B2 | 9/2023 | Schroers et al. |
| 11,766,786 B2 | 9/2023 | Cordoba et al. |
| 11,780,092 B2 | 10/2023 | Desai et al. |
| 11,785,938 B2 | 10/2023 | Clavien et al. |
| 11,786,329 B2 | 10/2023 | Fuerst et al. |
| 11,789,315 B1 | 10/2023 | Yu et al. |
| 11,793,500 B2 | 10/2023 | Vargas |
| 11,793,597 B2 | 10/2023 | Vargas et al. |
| 11,801,365 B2 | 10/2023 | Blackera et al. |
| 11,813,203 B2 | 11/2023 | Timm et al. |
| 11,819,295 B2 | 11/2023 | Wenderow et al. |
| 11,832,904 B2 | 12/2023 | Wenderow et al. |
| 11,844,580 B2 | 12/2023 | Sen et al. |
| 11,844,732 B2 | 12/2023 | Klem et al. |
| 11,883,119 B2 | 1/2024 | Sen et al. |
| 11,883,245 B2 | 1/2024 | Fathollahi Ghezelghieh et al. |
| 11,890,024 B2 | 2/2024 | Panian |
| 11,890,432 B2 | 2/2024 | Awad et al. |
| 11,896,325 B2 | 2/2024 | Clark et al. |
| 11,903,669 B2 | 2/2024 | Cope et al. |
| 11,906,009 B2 | 2/2024 | Klem |
| 11,910,997 B2 | 2/2024 | Fuerst et al. |
| 11,911,120 B2 | 2/2024 | Freiin von Kapri et al. |
| 11,911,910 B2 | 2/2024 | Gonenc et al. |
| 11,918,240 B2 | 3/2024 | Deville et al. |
| 11,918,312 B2 | 3/2024 | Yu |
| 11,918,423 B2 | 3/2024 | Kottenstette et al. |
| 11,998,290 B2 | 6/2024 | Murphy et al. |
| 12,004,829 B2 | 6/2024 | Searfoss et al. |
| 12,005,589 B2 | 6/2024 | Rea et al. |
| 12,035,989 B2 | 7/2024 | Clark et al. |
| 12,046,363 B2 | 7/2024 | Shrivastava et al. |
| 12,059,161 B2 | 8/2024 | Deville et al. |
| 12,059,225 B2 | 8/2024 | Zhou et al. |
| 12,076,036 B2 | 9/2024 | Baron et al. |
| 12,076,099 B2 | 9/2024 | Shrivastava et al. |
| 12,076,497 B2 | 9/2024 | Fantuzzi et al. |
| 12,076,505 B2 | 9/2024 | Haubert |
| 12,082,982 B2 | 9/2024 | Jhaveri et al. |
| 12,087,024 B2 | 9/2024 | Djelouah et al. |
| 12,102,290 B2 | 10/2024 | Sharon et al. |
| 12,114,940 B2 | 10/2024 | Garcia Kilroy et al. |
| 12,117,624 B2 | 10/2024 | Fuerst et al. |
| 12,133,700 B2 | 11/2024 | Miller et al. |
| 12,133,702 B2 | 11/2024 | Nowlin et al. |
| 12,133,965 B2 | 11/2024 | Chassot et al. |
| 12,137,990 B2 | 11/2024 | Walker et al. |
| 12,138,004 B2 | 11/2024 | Cone et al. |
| 12,138,130 B2 | 11/2024 | Garbus et al. |
| 12,144,564 B2 | 11/2024 | Barbagli et al. |
| 12,144,569 B2 | 11/2024 | Cone et al. |
| 12,144,575 B2 | 11/2024 | Torabi |
| 12,150,660 B1 | 11/2024 | Teigen et al. |
| 12,150,796 B2 | 11/2024 | Wenderow et al. |
| 12,156,666 B2 | 12/2024 | Trosper et al. |
| 12,156,667 B2 | 12/2024 | Trosper et al. |
| 12,156,711 B2 | 12/2024 | Liao et al. |
| 12,157,238 B2 | 12/2024 | Fredrickson et al. |
| 12,161,419 B2 | 12/2024 | Fuerst et al. |
| 12,171,505 B2 | 12/2024 | Barbagli et al. |
| 12,171,543 B2 | 12/2024 | Duindam et al. |
| 12,177,411 B2 | 12/2024 | Culman |
| 12,178,387 B2 | 12/2024 | McDowall et al. |
| 12,178,399 B2 | 12/2024 | Itkowitz et al. |

(56) References Cited

U.S. PATENT DOCUMENTS

| | | |
|---|---|---|
| 12,178,526 B2 | 12/2024 | McKenney et al. |
| 12,178,534 B2 | 12/2024 | Asadian et al. |
| 12,185,947 B2 | 1/2025 | Hart |
| 12,191,031 B2 | 1/2025 | Azizian et al. |
| 12,201,484 B2 | 1/2025 | Itkowitz et al. |
| 12,201,485 B2 | 1/2025 | McDowall et al. |
| 12,212,240 B2 | 1/2025 | Schulz |
| 12,232,838 B2 | 2/2025 | Lau et al. |
| 2002/0113501 A1 | 8/2002 | Doi |
| 2002/0192113 A1 | 12/2002 | Uffenheimer et al. |
| 2003/0071285 A1 | 4/2003 | Tsukernik |
| 2003/0100849 A1 | 5/2003 | Jang |
| 2003/0105451 A1 | 6/2003 | Westlund et al. |
| 2003/0114739 A1 | 6/2003 | Fuimaono et al. |
| 2003/0125673 A1 | 7/2003 | Houde et al. |
| 2004/0068248 A1 | 4/2004 | Mooney et al. |
| 2004/0097805 A1 | 5/2004 | Verard et al. |
| 2004/0143225 A1 | 7/2004 | Callan |
| 2005/0077225 A1 | 4/2005 | Usher et al. |
| 2005/0107667 A1 | 5/2005 | Danitz |
| 2005/0165276 A1 | 7/2005 | Belson et al. |
| 2005/0277912 A1 | 12/2005 | John |
| 2006/0011501 A1 | 1/2006 | Itou et al. |
| 2006/0095022 A1 | 5/2006 | Moll et al. |
| 2006/0200026 A1 | 9/2006 | Wallace et al. |
| 2006/0200191 A1 | 9/2006 | Zadno-Azizi |
| 2007/0060915 A1 | 3/2007 | Kucklick |
| 2007/0106208 A1 | 5/2007 | Uber et al. |
| 2007/0142824 A1 | 6/2007 | Devengenzo |
| 2007/0179473 A1 | 8/2007 | Masters et al. |
| 2007/0270639 A1 | 11/2007 | Long |
| 2008/0027464 A1 | 1/2008 | Moll et al. |
| 2008/0086051 A1 | 4/2008 | Voegele |
| 2008/0234631 A1 | 9/2008 | Reis |
| 2008/0262513 A1 | 10/2008 | Stahler et al. |
| 2008/0319387 A1 | 12/2008 | Amisar et al. |
| 2009/0076445 A1 | 3/2009 | Furnish |
| 2009/0131955 A1 | 5/2009 | Wenderow et al. |
| 2009/0153374 A1 | 6/2009 | Maw et al. |
| 2009/0171332 A1 | 7/2009 | Bonneau |
| 2009/0204078 A1 | 8/2009 | Mitchell et al. |
| 2009/0254083 A1 | 10/2009 | Wallace et al. |
| 2009/0264785 A1 | 10/2009 | Causevic et al. |
| 2010/0069833 A1 | 3/2010 | Wenderow et al. |
| 2010/0175701 A1 | 7/2010 | Reis et al. |
| 2010/0204712 A1 | 8/2010 | Mallaby |
| 2010/0204713 A1 | 8/2010 | Ruiz Morales |
| 2010/0280363 A1 | 11/2010 | Skarda et al. |
| 2010/0286756 A1 | 11/2010 | Dorn |
| 2011/0004223 A1 | 1/2011 | Leeflang |
| 2011/0015484 A1 | 1/2011 | Alvarez et al. |
| 2011/0144658 A1 | 6/2011 | Wenderow et al. |
| 2011/0238010 A1 | 9/2011 | Kirschenman et al. |
| 2011/0288544 A1 | 11/2011 | Verin et al. |
| 2011/0313318 A1 | 12/2011 | Rule et al. |
| 2012/0071895 A1 | 3/2012 | Stahler et al. |
| 2012/0172798 A1 | 7/2012 | Miller et al. |
| 2012/0179032 A1 | 7/2012 | Bromander et al. |
| 2012/0316458 A1 | 12/2012 | Rahmanv |
| 2013/0035537 A1 | 2/2013 | Wallace |
| 2013/0053704 A1 | 2/2013 | Bernak et al. |
| 2013/0096551 A1 | 4/2013 | Govari et al. |
| 2013/0131499 A1 | 5/2013 | Chan et al. |
| 2013/0214912 A1 | 8/2013 | Beyar et al. |
| 2013/0231678 A1 | 9/2013 | Wenderow |
| 2014/0058321 A1 | 2/2014 | Wenderow et al. |
| 2014/0066900 A1 | 3/2014 | Blacker |
| 2014/0150782 A1 | 6/2014 | Vazales |
| 2014/0163364 A1 | 6/2014 | Perers |
| 2014/0216250 A1 | 8/2014 | Meyer |
| 2014/0228762 A1 | 8/2014 | Capone |
| 2014/0276016 A1 | 9/2014 | Stigall |
| 2014/0276233 A1 | 9/2014 | Murphy |
| 2014/0276389 A1 | 9/2014 | Walker |
| 2014/0276948 A1 | 9/2014 | Zirps |
| 2014/0318702 A1 | 10/2014 | Tegg |
| 2015/0005738 A1 | 1/2015 | Blacker |
| 2015/0005745 A1 | 1/2015 | Bergman et al. |
| 2015/0073391 A1 | 3/2015 | Hutchins et al. |
| 2015/0088002 A1 | 3/2015 | Podhajsky |
| 2015/0157252 A1 | 6/2015 | Sabesan |
| 2015/0272683 A1 | 10/2015 | Yang et al. |
| 2015/0314105 A1 | 11/2015 | Gasparyan |
| 2015/0327875 A1 | 11/2015 | Look |
| 2015/0374483 A1 | 12/2015 | Janardhan |
| 2016/0058513 A1 | 3/2016 | Giorgi |
| 2016/0067448 A1* | 3/2016 | Blacker .................. A61B 34/25 604/95.01 |
| 2016/0074057 A1 | 3/2016 | Jezierski et al. |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |
| 2017/0027653 A1 | 2/2017 | Kirschenman |
| 2017/0135773 A1 | 5/2017 | Lohmeier et al. |
| 2017/0143416 A1 | 5/2017 | Guler et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0281288 A1 | 10/2017 | Au |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1 | 6/2018 | Yi et al. |
| 2018/0185104 A1 | 7/2018 | Olson et al. |
| 2018/0199916 A1 | 7/2018 | Sugihara et al. |
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0030324 A1 | 1/2019 | Grace et al. |
| 2019/0076640 A1 | 3/2019 | Bhatnagar et al. |
| 2019/0111237 A1 | 4/2019 | Cabiri et al. |
| 2019/0133666 A1 | 5/2019 | Johnson |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0336674 A1 | 11/2019 | Schermeier |
| 2019/0365485 A1 | 12/2019 | Kottenstette et al. |
| 2019/0380825 A1* | 12/2019 | Perkins ............... A61F 2/954 |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0028181 A1 | 1/2020 | Arugula et al. |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170630 A1 | 6/2020 | Wong et al. |
| 2020/0242767 A1 | 7/2020 | Zhao et al. |
| 2020/0282186 A1 | 9/2020 | Blacker et al. |
| 2020/0289219 A1 | 9/2020 | Denlinger et al. |
| 2020/0297444 A1 | 9/2020 | Camarillo et al. |
| 2020/0297973 A1 | 9/2020 | Blacker et al. |
| 2020/0306064 A1 | 10/2020 | Perkins et al. |
| 2020/0316340 A1 | 10/2020 | Wenderow et al. |
| 2020/0324084 A1 | 10/2020 | Falb et al. |
| 2020/0338308 A1 | 10/2020 | Saber et al. |
| 2020/0345979 A1* | 11/2020 | Loh ................... A61M 25/0041 |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0376249 A1 | 12/2020 | Lockhart |

(56) References Cited

U.S. PATENT DOCUMENTS

| | | |
|---|---|---|
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2020/0405950 A1 | 12/2020 | Burren |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0046284 A1 | 2/2021 | Mauch |
| 2021/0060767 A1 | 3/2021 | Guerrera et al. |
| 2021/0068852 A1 | 3/2021 | Spence |
| 2021/0077211 A1 | 3/2021 | Blacker et al. |
| 2021/0093406 A1 | 4/2021 | Blacker et al. |
| 2021/0100980 A1 | 4/2021 | Blacker |
| 2021/0145532 A1 | 5/2021 | Tucker et al. |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0192759 A1 | 6/2021 | Lang |
| 2021/0196242 A1 | 7/2021 | Perez |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0247396 A9 | 8/2021 | Penny et al. |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0315596 A1 | 10/2021 | Buck et al. |
| 2021/0353129 A1 | 11/2021 | Roelle et al. |
| 2021/0361366 A1 | 11/2021 | Murphy et al. |
| 2021/0369370 A1 | 12/2021 | Malanoski |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168049 A1 | 6/2022 | Tanner et al. |
| 2022/0211452 A1 | 7/2022 | Clark et al. |
| 2022/0233263 A1 | 7/2022 | Canale et al. |
| 2022/0233264 A1 | 7/2022 | Klem |
| 2022/0233820 A1 | 7/2022 | Clark et al. |
| 2022/0241490 A1 | 8/2022 | Marass |
| 2022/0313375 A1 | 10/2022 | Zhang et al. |
| 2022/0323096 A1 | 10/2022 | Naglretter et al. |
| 2022/0331509 A1 | 10/2022 | Buck et al. |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |
| 2023/0035508 A1 | 2/2023 | Clark et al. |
| 2023/0035946 A1 | 2/2023 | Kapadia |
| 2023/0043432 A1 | 2/2023 | Kapadia |
| 2023/0046468 A1 | 2/2023 | Lau et al. |
| 2023/0048388 A1 | 2/2023 | Lau et al. |
| 2023/0052862 A1 | 2/2023 | Lau et al. |
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0209018 A1 | 6/2023 | Alexanderson et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2023/0380914 A1 | 11/2023 | Meglan et al. |
| 2023/0380915 A1 | 11/2023 | Hundertmark |
| 2024/0001101 A1 | 1/2024 | Wallin et al. |
| 2024/0016560 A1* | 1/2024 | Canale .......... A61B 34/70 |
| 2024/0019042 A1 | 1/2024 | Lim |
| 2024/0032949 A1 | 2/2024 | Yang et al. |
| 2024/0033017 A1 | 2/2024 | Yang et al. |
| 2024/0033018 A1 | 2/2024 | Yang et al. |
| 2024/0033019 A1 | 2/2024 | Lau et al. |
| 2024/0033486 A1 | 2/2024 | Lau et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0122612 A1 | 4/2024 | Bartholomew |
| 2024/0138862 A1 | 5/2024 | Beach |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180643 A1 | 6/2024 | Lau et al. |
| 2024/0180650 A1 | 6/2024 | Lau et al. |
| 2024/0180651 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181214 A1 | 6/2024 | Lau et al. |
| 2024/0181224 A1 | 6/2024 | Lau et al. |
| 2024/0181298 A1 | 6/2024 | Lau et al. |
| 2024/0183382 A1 | 6/2024 | Lau et al. |
| 2024/0197416 A1 | 6/2024 | Gonzalez |
| 2024/0197418 A1 | 6/2024 | Jourdan |
| 2024/0198051 A1 | 6/2024 | Jourdan |
| 2024/0207570 A1 | 6/2024 | Mar |
| 2024/0382668 A1 | 11/2024 | Bartholomew et al. |
| 2024/0398495 A1 | 12/2024 | Lee et al. |
| 2025/0032201 A1 | 1/2025 | Bartholomew et al. |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |

(56) References Cited

FOREIGN PATENT DOCUMENTS

| | | |
|---|---|---|
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2022/048984 | 3/2022 |
| WO | WO 2022/154979 | 7/2022 |

OTHER PUBLICATIONS

US 12,108,960 B1, 10/2024, Teigen et al. (withdrawn)
Bergman et al "Robotic Assisted Percutaneous Coronary Intervention"; Handbook of Robotic and Image-Guided Surgery; 22 pages (Year: 2020).*
Bao et al., Apr. 2018, Operation evaluation in-human of a novel remote-controlled vascular interventional robot, Biomedical Microdevices, 20(2):34.
Bao et al., Feb. 2018, A cooperation of catheters and guidewires-based novel remote-controlled vascular interventional robot, Biomedical Microdevices, 20(1):20.
Bell, Apr. 4, 2019, Coding for Empathy, https://www.youtube.com/watch?v=13tzbxofDVc, screenshot of video.
Bency et al., Apr. 25, 2019, Neural Path Planning: Fixed Time, Near-Optimal Path Generation via Oracle Imitation, arXiv:1904.11102v1 [cs.RO], 8 pp.
Chen et al., Feb. 14, 2020, Deep learning robotic guidance for autonomous vascular access, Nature Machine Intelligence, https://doi.org/10.1038/s42256-020-0148-7, 12 pp.
Das et al., Feb. 21, 2019, Learning-Based Proxy Collision Detection for Robot Motion Planning Applications, arXiv:1902.08164v1 [cs.RO], 19 pp.
Das et al., May 29, 2020, Stochastic Modeling of Distance to Collision for Robot Manipulators, arXiv:2005.14391v1 [cs.RO], 8 pp.
Evard, Jun. 2018, Catheter localization utilizing a sensor-enabled guidewire design of a proof-of- concept system, Masters Thesis, California Polytechnic State University, San Luis Obispo, 186 pp.
Fagogenis et al., Apr. 2019, Autonomous Robotic Intracardiac Catheter Navigation Using Haptic Vision, Science Robotics, 4(29):1-12.
Guo et al., Apr. 13, 2018, Study on real-time force feedback for a master-slave interventional surgical robotic system, Biomedical Microdevices, 20(2):37, 12 pp.
Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.
Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.
Jiang et al., 2018, Initial clinical trial of robot of endovascular treatment with force feedback and cooperating of catheter and guidewire, Applied Bionics and Biomechanics, vol. 2018, Article ID 9735979, 10 pp.
Johnson et al., Aug. 12, 2020, Dynamically Constrained Motion Planning Networks for Non-Holonomic Robots, arXiv:2008.05112v1 [cs.RO}, 7 pp.
Kagiyama et al., Jul. 31, 2019, First experience of robotic-assisted percutaneous coronary intervention in Japan, Intern Med Advance Publication, doi: 10/2016/internalmedicine.3272-19.
Kuang et al., Apr. 2020, Vibration-Based Multi-Axis Force Sensing: Design, Characterization, and Modeling, IEEE Robotics and Automation Letters, 5(2):3082-3089.
Li et al., 2022, An endovascular catheterization robotic system using collaborative operation with magnetically controlled haptic force feedback, Micromachines, 13:505.
Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.
Liu et al., 2021, Animal experiment of a novel neurointerventional surgical robotic system with master-slave mode, Applied Bionics and Biomechanics, vol. 2021, Article ID 8836268, 8 pp.
Qureshi et al., Feb. 2021, Motion Planning Networks: Bridging the Gap Between Learning-Based and Classical Motion Planners, IEEE Transactions on Robotics, 37(1), 19 pp.

(56) References Cited

OTHER PUBLICATIONS

Qureshi et al., Jul. 3, 2021, Constrained Motion Planning Networks X, arXiv:2010.08702v2 [cs.RO], 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi.org/10.1007/s00542-018-03750-4.

Wilcox et al., Jan. 2020, SOLAR-GP: Sparse Online Locally Adaptive Regression Using GaussianProcesses for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

International Search Report and Written Opinion dated Jan. 22, 2024 in application No. PCT/US23/29109.

International Search Report and Written Opinion dated Jan. 22, 2024 in application No. PCT/US23/29106.

International Search Report and Written Opinion dated Jan. 3, 2024 in application No. PCT/US23/29108.

\* cited by examiner

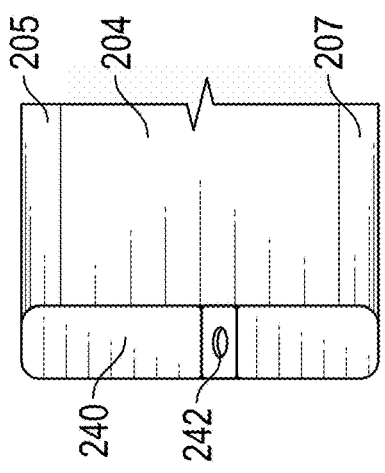
FIG. 3K
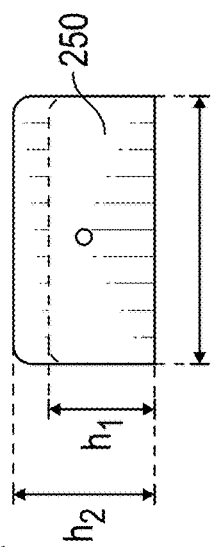
FIG. 3L
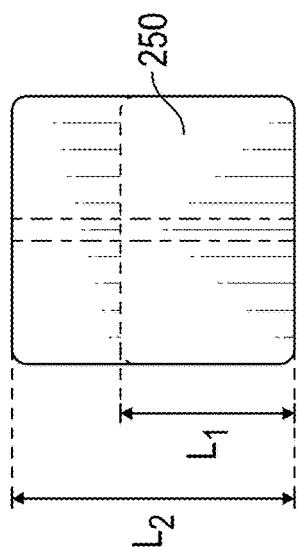
FIG. 3M
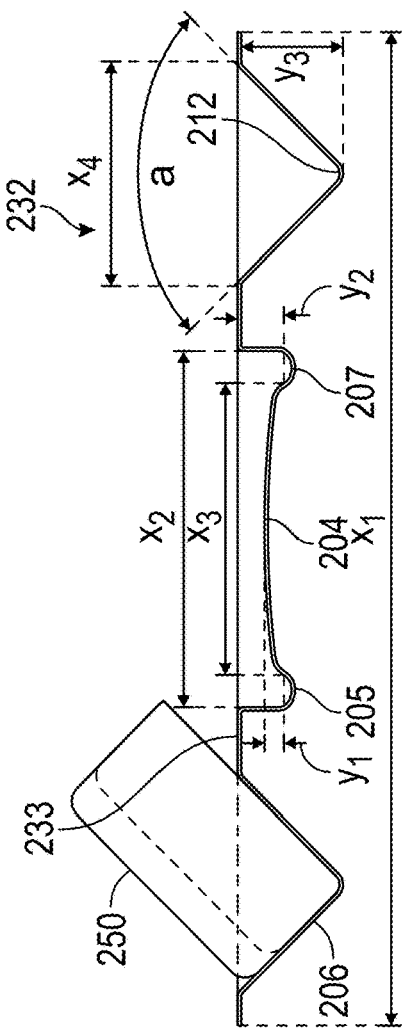
FIG. 3G
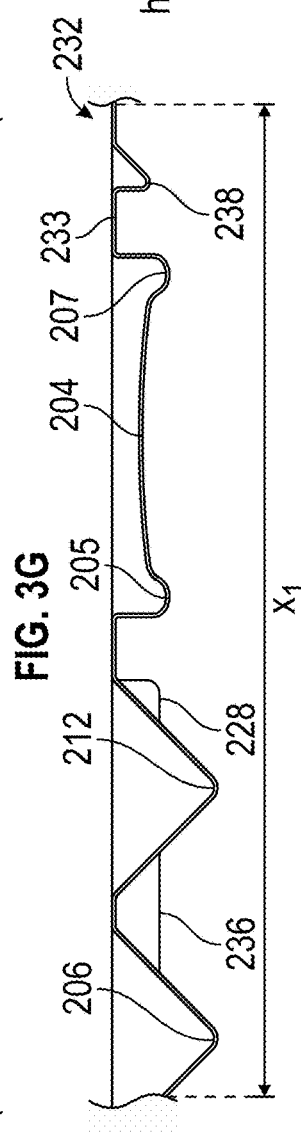
FIG. 3H
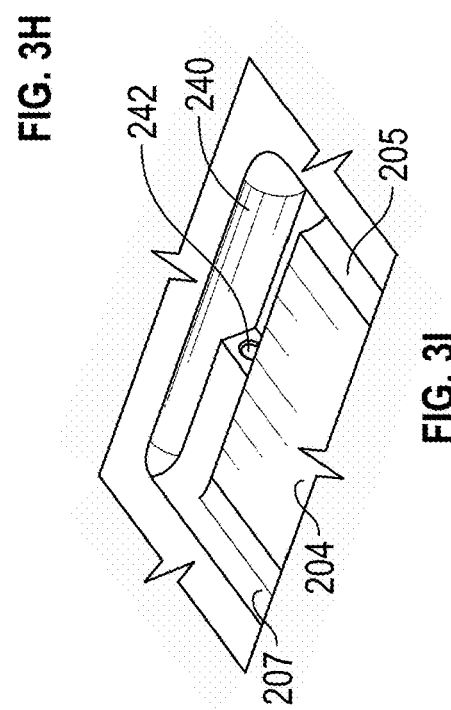
FIG. 3J
FIG. 3I Side View of Puck and Carriage Equivalent System

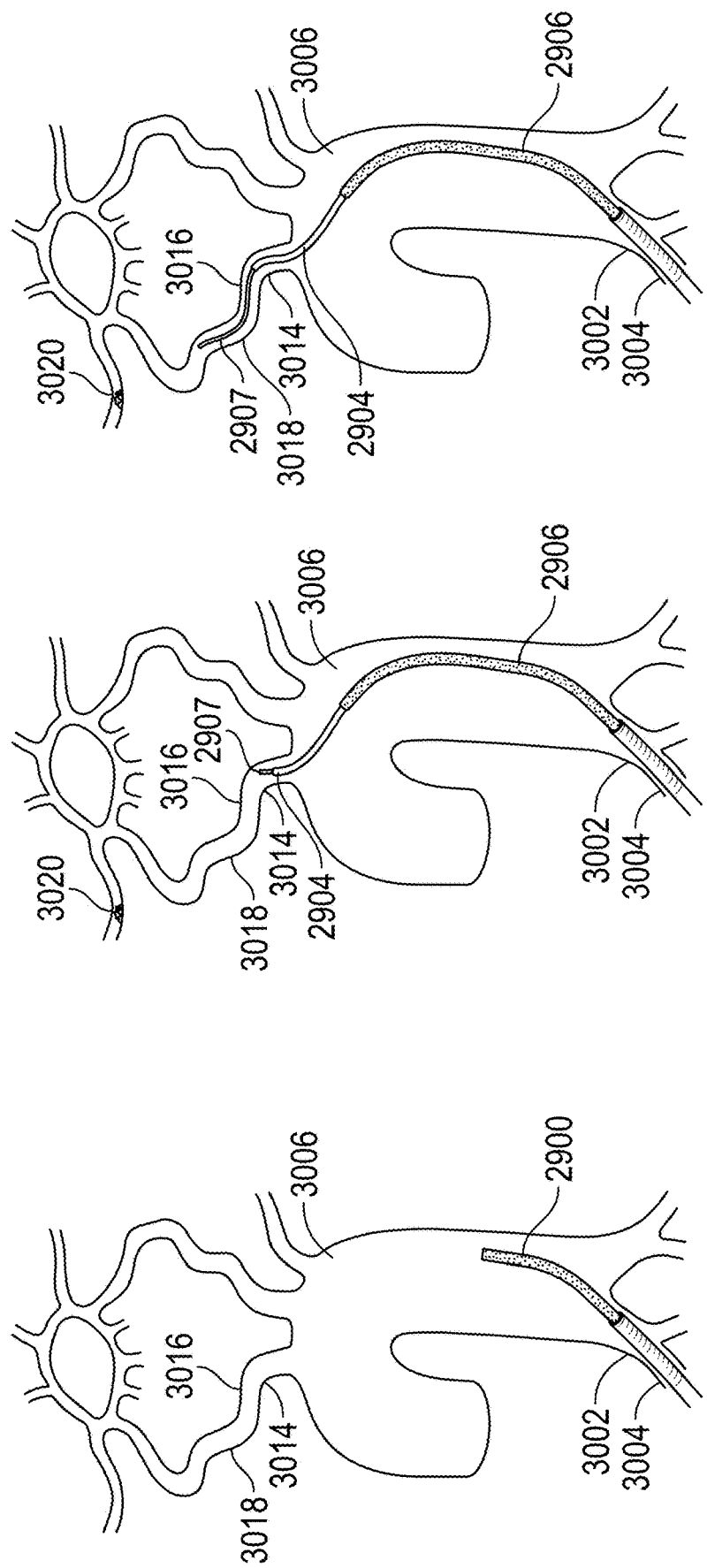

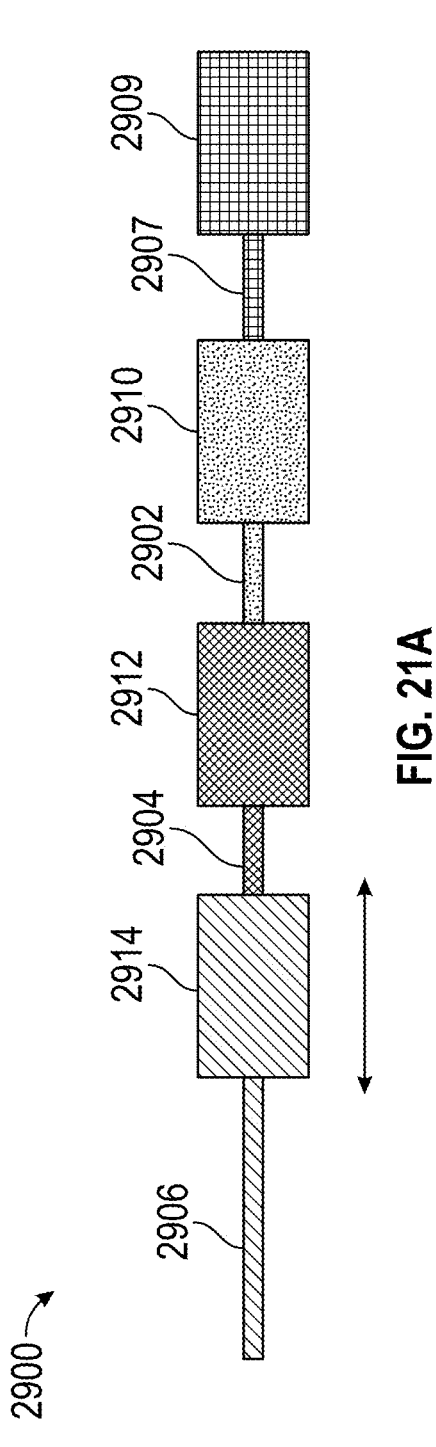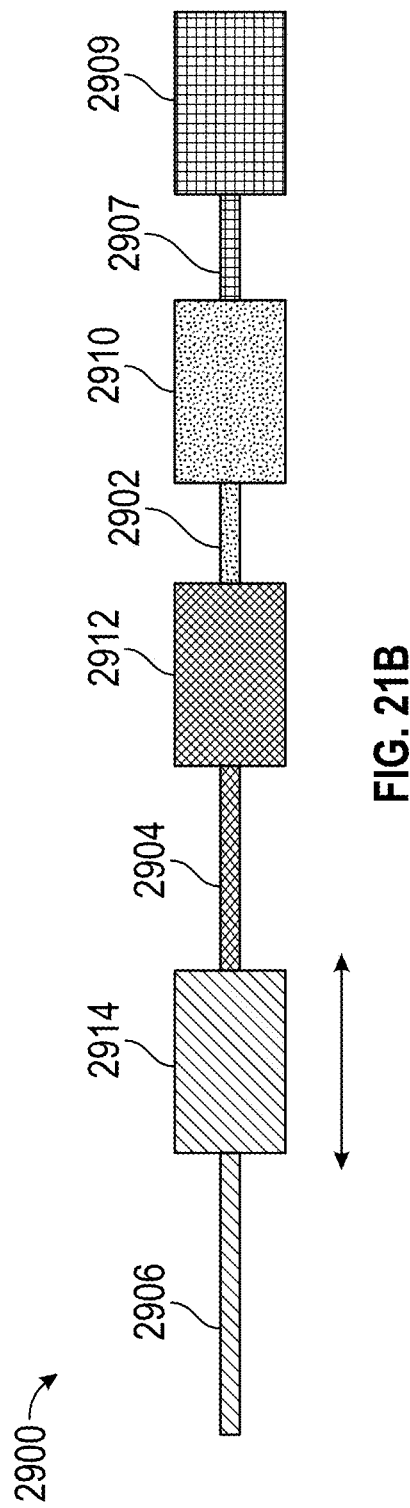

ROBOTIC DRIVE SYSTEM FOR ACHIEVING SUPRA-AORTIC ACCESS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application is a continuation-in-part of U.S. application Ser. No. 17/816,669, filed on Aug. 1, 2022, titled METHOD OF SUPRA-AORTIC ACCESS FOR A NEUROVASCULAR PROCEDURE, the entire content of which is incorporated by reference herein for all purposes and forms a part of this specification.

BACKGROUND

Field

The present application relates to neurovascular procedures, and more particularly, to catheter assemblies and robotic control systems for neurovascular site access.

Description of the Related Art

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neurointerventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due energy storage and release caused by frictional interplay between coaxial shafts and the patient's vasculature. Supra-aortic access necessary to reach the neurovascular is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

There is provided in accordance with one aspect of the present disclosure a supra-aortic access robotic control system. The system comprises a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter. The access catheter hub may also laterally deflect a distal deflection zone of the access catheter. The guidewire hub may additionally be configured to laterally deflect a distal portion of the guidewire.

There may also be provided a procedure catheter hub configured to manipulate a procedure catheter. Following robotic placement of the guidewire, access catheter and guide catheter such that the guide catheter achieves supra aortic access, the guidewire and access catheter may be proximally withdrawn and the procedure catheter advanced through and beyond the guide catheter, with or without guidewire support (said guidewire may be smaller in diameter and/or more flexible than the guidewire used to gain supra aortic access), to reach a more distal neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, an ablation catheter, an RF ablation catheter or guidewire, a balloon catheter, or a microcatheter used to deliver a stent retriever, a balloon catheter or a stent retriever.

The control system may further comprise a driven magnet on each of a guidewire hub, an access catheter hub and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may comprise a tray made from a thin polymer membrane, or any membrane of non-ferromagnetic material.

The control system may further comprise a control console which may be connected to the support table or may be located remotely from the support table. The position of each driven magnet and corresponding hub is movable in response to manual manipulation of a guidewire drive control, access catheter drive control, or procedure catheter drive control on the console or on a particular controller not associated with the console.

The control system may further comprise a processor for controlling the position of the drive magnets. The processor may be in wired communication with the control console, or in wireless communication with the control console. The driven magnets may be configured to remain engaged with the corresponding drive magnets until application of an axial disruption force of at least about 300 grams.

There is also provided a robotically driven interventional device. The device comprises an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. In some embodiments, at least one control element may be an axially movable tubular body or fiber, ribbon, or wire such as a pull wire extending through the interventional device to, for example, a distal deflection zone. In some embodiments, any number of control elements may be advanced, retracted, or otherwise moved in a similar manner.

There is also provided a control system for controlling movement of interventional devices. In one configuration, the control system comprises a guidewire control, configured to control axial travel and rotation of a guidewire; an access catheter control, configured to control axial and rotational movement of an access catheter; and a guide catheter control, configured to control axial movement and/or rotation of a guide catheter.

The control system may further comprise a deflection control, configured to control deflection of the access catheter or procedure catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further comprise a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further comprise a graphical user interface with at least one display for indicating the status of at least one device parameter, and/or indicating the status of at least one patient parameter.

There is also provided a sterile packaging assembly for transporting interventional devices to a robotic surgery site. The packaging assembly may comprise a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient, with an upper surface of the base within a sterile field and a lower surface of the base outside of the sterile field.

Any of the hubs disclosed herein may further comprise a fluid injection port and/or a wireless RF transceiver for communications and/or power transfer. The hub may comprise a visual indicator, for indicating the presence of a clot. In some embodiments, the hub may also comprise wired electrical communications and power port. The visual indicator may comprise a clot chamber having a transparent window. A filter may be provided in the clot chamber.

Any of the hubs disclosed herein may further comprise a sensor for detecting a parameter of interest such as the presence of a clot. The sensor, in some instances, may be positioned on a flexible body. The sensor may comprise a pressure sensor or an optical sensor. In some embodiments, the sensor may comprise one or more of a force sensor, a positioning sensor, a temperature sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each comprise one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method comprises the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally comprise advancing the procedure catheter hub to position a distal end of the procedure catheter at a neurovascular treatment site. The driving the access catheter step may comprise driving the access catheter distally through a guide catheter. The driving the access catheter step may include the step of laterally deflecting a distal region of the access catheter to achieve supra-aortic access. In some embodiments, the driving the access catheter step may also include rotating the access catheter.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guidewire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may comprise magnetically coupling a hub on each of the guidewire, access catheter and guide catheter, to separate corresponding couplers carrying corresponding drive magnets independently movably carried by the drive table. The procedure assembly may comprise a guidewire, a first catheter and a second catheter. The guidewire and first catheter may be positioned concentrically within the second catheter. The procedure assembly may be advanced as a unit through at least a portion of the length of the guide catheter, and the procedure may comprise a neurovascular thrombectomy.

There is also provided a method of performing a neurovascular procedure. The method includes the steps of providing a multi-catheter assembly including an access catheter, a guide catheter, and a procedure catheter, coupling the assembly to a robotic drive system, driving the assembly to achieve supra-aortic access, driving a subset of the assembly to a neurovascular site, wherein the subset includes the guide catheter and the procedure catheter, proximally removing the access catheter, and performing a neurovascular procedure using the procedure catheter.

The neurovascular procedure can include a neurovascular thrombectomy. The assembly may further include a guidewire, wherein each of the guidewire, the access catheter, the guide catheter, and the procedure catheter are configured to be adjusted by a respective hub. Coupling the assembly to the robotic drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The first drive magnet, the second drive magnet, the third drive magnet, and the fourth drive magnet can each be independently movably carried by a drive table. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

There is also provided a method of performing a neurovascular procedure. The method includes the steps of providing an assembly including a guidewire, an access catheter, a guide catheter, and a procedure catheter coaxially moveably assembled into a single multi-catheter assembly, coupling the assembly to a drive system, driving the assembly to achieve supra-aortic access, driving a subset of the assembly to an intracranial site, wherein the subset includes the guidewire, the guide catheter, and the procedure catheter, and performing a neurovascular procedure using the subset of the assembly.

Each of the guidewire, the access catheter, the guide catheter, and the procedure catheter can be configured to be adjusted by a respective hub. Coupling the assembly to the drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The drive system can be a robotic drive system, and the first drive magnet, the second drive magnet, the third drive magnet, and the fourth drive magnet can each be independently movably carried by a drive table associated with the robotic drive system. The first drive magnet, the second drive magnet, the third drive magnet, and the fourth drive magnet can each be independently movably carried by a drive table.

There is also provided a method of performing a neurovascular procedure. The method includes providing an assembly including a guidewire having a guidewire hub, an access catheter having an access catheter hub, and a guide catheter having a guide catheter hub. The method also includes coupling the guidewire hub to a first hub adapter, the access catheter hub to a second hub adapter, and the guide catheter hub to a third hub adapter, wherein each of the first hub adapter, the second hub adapter and the third hub adapter is movably carried by a support table. The method also includes driving the assembly in response to movement of each of the first hub adapter, the second hub adapter and the third hub adapter along the support table until the assembly is positioned to achieve supra-aortic vessel access.

The method can include the step of driving a subset of the assembly along the support table until the subset of the assembly is positioned to perform a neurovascular procedure at a neurovascular treatment site, wherein the subset of the assembly includes the guidewire, the guide catheter, and a procedure catheter. The neurovascular procedure can include a thrombectomy. Coupling the guidewire hub to the first hub adapter can include magnetically coupling the guidewire hub to a first drive magnet. Coupling the access catheter hub to the second hub adapter can include magnetically coupling the access catheter hub to a second drive magnet. Coupling the guide catheter hub to the third hub adapter can include magnetically coupling the guide catheter hub to a third drive magnet. The first drive magnet, the second drive magnet and the third drive magnets can be independently movably carried by the support table. The first drive magnet can be coupled to a first driven magnet across a sterile field barrier. The second drive magnet can be coupled to a second driven magnet across the sterile field barrier. The third drive magnet can be coupled to a third driven magnet across the sterile field barrier. Coupling the guidewire hub to the first hub adapter can include mechanically coupling the guidewire hub to a first drive. Coupling the access catheter hub to the second hub adapter can include mechanically coupling the access catheter hub to a second drive. Coupling the guide catheter hub to the third hub adapter can include mechanically coupling the guide catheter hub to a third drive. The guidewire and the guide catheter can be advanced as a unit along at least a portion of a length of the access catheter after supra-aortic access is achieved. The guidewire hub can be configured to adjust an axial position and a rotational position of the guidewire. The assembly can further include a procedure catheter having a procedure catheter hub. The procedure catheter hub can be configured to adjust an axial position and a rotational position of the procedure catheter. The procedure catheter hub can be further configured to laterally deflect a distal deflection zone of the procedure catheter. The guidewire hub can be configured to adjust an axial position and a rotational position of the guidewire. The procedure catheter hub can be configured to adjust an axial position and a rotational position of the procedure catheter. The guide catheter hub can be configured to adjust an axial position of the guide catheter. The access catheter hub can be configured to adjust an axial position and a rotational position of the access catheter. The procedure catheter hub can be further configured to laterally deflect a distal deflection zone of the procedure catheter. The access catheter hub can be further configured to laterally deflect a distal deflection zone of the access catheter. The guide catheter hub can be configured to adjust an axial position of the guide catheter. The access catheter hub can be configured to adjust an axial position and a rotational position of the access catheter. The access catheter hub can be further configured to laterally deflect a distal deflection zone of the access catheter.

There is also provided a drive system for achieving supra-aortic access and neurovascular treatment site access. The system includes a guidewire hub configured to adjust an axial position and a rotational position of a guidewire, a procedure catheter hub configured to adjust an axial position and a rotational position of a procedure catheter, a guide catheter hub configured to adjust an axial position of a guide catheter, and an access catheter hub configured to adjust an axial position and a rotational position of an access catheter, the access catheter further configured to laterally deflect a distal deflection zone of the access catheter.

The procedure catheter hub can be further configured to laterally deflect a distal deflection zone of the procedure catheter. The guidewire hub can be configured to couple to a guidewire hub adapter by magnetically coupling the guidewire hub to a first drive magnet. The access catheter hub can be configured to couple to an access catheter hub adapter by magnetically coupling the access catheter hub to a second drive magnet. The guide catheter hub can be configured to couple to a guide catheter hub adapter by magnetically coupling the guide catheter hub to a third drive magnet. The procedure catheter hub can be configured to couple to a procedure catheter hub adapter by magnetically coupling the procedure catheter hub to a fourth drive magnet. The first drive magnet, the second drive magnet, the third drive magnet, and the fourth drive magnet can be independently movably carried by a drive table. The system can include first driven magnet on the guidewire hub configured to cooperate with the first drive magnet such that the first driven magnet moves in response to movement of the first drive magnet. The first drive magnet can be configured to move outside of a sterile field while separated from the first driven magnet by a sterile field barrier while the first driven magnet is within the sterile field. A position of the first drive magnet can be movable in response to manipulation of a procedure drive control on a control console in electrical communication with the drive table. The system can include a second driven magnet on the access catheter hub configured to cooperate with the second drive magnet such that the second driven magnet is configured to move in response to movement of the second drive magnet, wherein the second drive magnet is configured to move outside of the sterile field while separated from the second driven magnet by the barrier while the second driven magnet is within the sterile field. The system can include a third driven magnet on the guide catheter hub configured to cooperate with the third drive magnet such that the third driven magnet is configured to move in response to movement of the third drive magnet, wherein the third drive magnet is configured to move outside of the sterile field while separated from the third driven magnet by the barrier while the third driven magnet is within the sterile field. The system can include a fourth driven magnet on the procedure catheter hub configured to cooperate with the fourth drive magnet such that the fourth driven magnet is configured to move in response to movement of the fourth drive magnet, wherein the fourth drive magnet is configured to move outside of the sterile field while separated from the fourth driven magnet by the barrier while the fourth driven magnet is within the sterile field. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a balloon catheter. The procedure catheter can be a catheter to facilitate percutaneous valve repair or replacement. The procedure catheter can be an ablation catheter.

There is also provided method of achieving supra-aortic access and neurovascular treatment site access. The method includes the steps of providing a drive system including a guidewire hub configured to adjust an axial position and a rotational position of a guidewire, a procedure catheter hub configured to adjust an axial position and a rotational position of a procedure catheter; a guide catheter hub configured to adjust an axial position of a guide catheter, and an access catheter hub configured to adjust an axial position and a rotational position of an access catheter, the access catheter further configured to laterally deflect a distal deflection zone of the access catheter, and moving at least one of the guidewire hub, the procedure catheter hub, the guide catheter hub, and the access catheter hub to drive movement of at least one of the guidewire, the procedure catheter, the guide catheter, and the access catheter. The method can further include controlling the procedure catheter hub to laterally deflect a distal deflection zone of the procedure catheter.

There is also provided a method of achieving supra aortic access. The method includes the steps of providing an assembly including a guidewire, an access catheter and a guide catheter, coaxially moveably assembled into a single multi-catheter assembly, coupling the assembly to a drive system, driving the assembly to an aortic arch, and advancing the access catheter to achieve supra-aortic access to a branch vessel off of the aortic arch.

The method can further include driving a subset of the assembly to an intracranial site, and performing a neurovascular procedure using the subset of the assembly. The subset can include the guidewire, the guide catheter, and a procedure catheter. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter. The intracranial procedure can include an intracranial thrombectomy. The neurovascular procedure can include a neurovascular thrombectomy. At least one of the guidewire, the access catheter, and the guide catheter can include a hub configured to couple to a robotic drive system. Coupling the assembly to the drive system can include magnetically coupling a guide catheter hub to the drive system. Coupling the assembly to the drive system can include mechanically coupling a guide catheter hub to the drive system. The drive system can be a robotic drive system, and at least a first drive magnet, a second drive magnet, and a third drive magnet are each independently movably carried by a drive table associated with the robotic drive system.

There is also provided a method of priming an interventional device assembly. The method includes providing the interventional device assembly, the interventional device assembly including a first interventional device coupled to a first hub and a second interventional device coupled to a second hub arranged in a concentric stack, the second interventional device being positioned within a lumen of the first interventional device. The method includes coupling the interventional device assembly to a drive system while arranged in the concentric stack, axially advancing the first interventional device and the first hub relative to the second hub to decrease a depth of insertion of the second interventional device within the lumen of the first interventional device while maintaining a distal end of the second interventional device within the lumen of the first interventional device, and flushing the first interventional device with fluid after decreasing the depth of insertion of the second interventional device within the lumen of the first interventional device.

The first interventional device can be a first catheter and the second interventional device can be a second catheter. The first catheter can be a guide catheter, the first hub can be a guide catheter hub, the second catheter can be a procedure catheter, and the second hub can be a procedure catheter hub. The interventional device assembly can include an access catheter coupled to an access catheter hub arranged in the concentric stack, the access catheter being positioned within a lumen of the procedure catheter. The method can include returning the guide catheter to an initial position relative to the procedure catheter after flushing the guide catheter with fluid, axially advancing the guide catheter, the guide catheter hub, the procedure catheter, and the procedure catheter hub relative to the access catheter hub to decrease a depth of insertion of the access catheter within the lumen of the procedure catheter while maintaining a distal end of the access catheter within the lumen of the procedure catheter and substantially maintaining a relative position between the guide catheter and the procedure catheter, and flushing the procedure catheter with fluid after decreasing the depth of insertion of the access catheter within the lumen of the procedure catheter. The interventional device assembly can include a guidewire coupled to a guidewire hub arranged in the concentric catheter stack, the guidewire being positioned within a lumen of the access catheter. The method can include returning the guide catheter and the procedure catheter to an initial position relative to the access catheter after flushing the procedure catheter with fluid, axially advancing the guide catheter, the guide catheter hub, the procedure catheter, the procedure catheter hub, the access catheter, and the access catheter hub relative to the guidewire hub to decrease a depth of insertion of the guidewire within the lumen of the access catheter while maintaining a distal end of the guidewire within the lumen of the access catheter and substantially maintaining relative positions between the guide catheter, the procedure catheter, and the access catheter, and flushing the access catheter with fluid after decreasing the depth of insertion of the guidewire within the lumen of the access catheter. The method can include flushing the second catheter with fluid, wherein the steps of flushing the first catheter and flushing the second catheter are performed simultaneously. The drive system can be a robotic drive system. The fluid can be saline. The first interventional device can be a catheter and the second interventional device can be a guidewire. The method can include reciprocally moving at least one of the first interventional device and the second interventional device relative to the other of the first interventional device and the second interventional device while flushing the first interventional device with fluid after decreasing the depth of insertion of the second interventional device within the lumen of the first interventional device.

There is also provided a method of priming a multi catheter assembly. The method includes providing the multi catheter assembly, the multi catheter assembly including a guidewire, an access catheter, a procedure catheter, and a guide catheter in a concentric stacked configuration, coupling the multi catheter assembly to a drive system, translating the guide catheter distally relative to the guidewire, the access catheter, and the procedure catheter, flushing the guide catheter with fluid, and translating the guide catheter proximally towards the guidewire, the access catheter, and the procedure catheter.

The method can include translating the procedure catheter and the guide catheter distally relative to the guidewire and the access catheter, flushing the procedure catheter with fluid, and translating the procedure catheter and the guide catheter proximally towards the guidewire and the access catheter. The method can include translating the access catheter, the procedure catheter, and the guide catheter distally relative to the guidewire, flushing the access catheter with fluid, and translating the access catheter, the procedure catheter, and the guide catheter proximally towards the guidewire. The fluid can be saline. The drive system can be a robotic drive system. The guidewire can coupled to a guidewire hub. The access catheter can be coupled to an access catheter hub. The procedure catheter can be coupled to a procedure catheter hub. The guide catheter can be coupled to a guide catheter hub. In the concentric stacked configuration, the procedure catheter is positioned within a lumen of the guide catheter, the access catheter is positioned within a lumen of the procedure catheter, and the guidewire is positioned within a lumen of the access catheter. The method can include reciprocally moving at least one of the guide catheter and the procedure catheter relative to the other of the guide catheter and the procedure catheter while flushing the guide catheter with fluid.

There is also provided a method of priming an interventional device assembly. The method includes providing the interventional device assembly, the interventional device assembly comprising a first interventional device and a second interventional device, the second interventional device being positioned within the first interventional device, and reciprocally moving at least one of the first interventional device and the second interventional device relative to the other of the first interventional device and the second interventional device while flushing a lumen between the first interventional device and the second interventional device with fluid to remove microbubbles from the lumen.

Reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device. Reciprocally moving at least one of the first interventional device and the second interventional device relative to the other of the first interventional device and the second interventional device can further include rotationally reciprocally moving at least one of the first interventional device and the second interventional device relative to the other of the first interventional device and the second interventional device. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length between about 10 mm and about 250 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length between about 25 mm and about 125 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length greater than 20 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device at a reciprocation frequency of no more than about 5 Hz. The reciprocation frequency can be no more than about 1 Hz. Reciprocally moving at least one of the first interventional device and the second interventional device relative to the other of the first interventional device and the second interventional device can include rotationally reciprocally moving at least one of the first interventional device and the second interventional device relative to the other of the first interventional device and the second interventional device. Reciprocally moving at least one of the first interventional device and the second interventional device relative to the other of the first interventional device and the second interventional device can include reciprocally moving both the first interventional device and the second interventional device relative to one another. Reciprocally moving at least one of the first interventional device and the second interventional device relative to the other of the first interventional device and the second interventional device can be performed by a robotic drive table. The first interventional device can be a first catheter and the second interventional device can be a second catheter. The first interventional device can be a catheter and the second interventional device can be a guidewire.

There is also provided a method of priming a multi catheter assembly. The method includes providing the multi catheter assembly, the multi catheter assembly including a guidewire, an access catheter, a procedure catheter, and a guide catheter arranged in a concentric catheter stack, wherein the guidewire is positioned within a lumen of the access catheter, the access catheter is positioned within a lumen of the procedure catheter, and the procedure catheter is positioned within a lumen of the guide catheter, and flushing the guide catheter with saline while reciprocally moving at least one of the guide catheter and the procedure catheter relative to the other of the guide catheter and the procedure catheter.

Flushing the guide catheter with saline while reciprocally moving at least one of the guide catheter and the procedure catheter relative to the other of the guide catheter and the procedure catheter can include axially reciprocally moving, rotationally reciprocally moving, or both axially and rotationally reciprocally moving at least one of the guide catheter and the procedure catheter relative to the other of the guide catheter and the procedure catheter. The method can include flushing the procedure catheter with saline while reciprocally moving at least one of the procedure catheter and the access catheter relative to the other of the procedure catheter and the access catheter. Flushing the procedure catheter with saline while reciprocally moving at least one of the procedure catheter and the access catheter relative to the other of the procedure catheter and the access catheter can include axially reciprocally moving, rotationally reciprocally moving, or both axially and rotationally reciprocally moving at least one of the procedure catheter and the access catheter relative to the other of the procedure catheter and the access catheter. The method can include flushing the access catheter with saline while reciprocally moving at least one of the access catheter and the guidewire relative to the other of the access catheter and the guidewire. Flushing the access catheter with saline while reciprocally moving at least one of the access catheter and the guidewire can include axially reciprocally moving, rotationally reciprocally moving, or both axially and rotationally reciprocally moving at least one of the access catheter and the guidewire relative to the other of the access catheter and the guidewire. The steps of flushing the guide catheter with saline while reciprocally moving at least one of the guide catheter and the procedure catheter relative to the other of the guide catheter and the procedure catheter, flushing the procedure catheter with saline while reciprocally moving at least one of the procedure catheter and the access catheter relative to the other of the procedure catheter and the access catheter, and flushing the access catheter with saline while reciprocally moving at least one of the access catheter and the guidewire relative to the other of the access catheter and the guidewire can be performed simultaneously.

BRIEF DESCRIPTION OF THE DRAWINGS

FIGS. 3G-3K show embodiments of an alternate sterile barrier having a convex drive surface.

FIGS. 3L and 3M depict an example of a hub that may be used with the sterile barriers of FIGS. 3G-3K.

FIGS. 18A-18E depict an example sequence of steps of introducing a catheter assembly configured to achieve supra-aortic access and neurovascular site access.

FIGS. 21A-21B depict an example sequence of steps of priming a catheter assembly in a stacked configuration.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table is positioned over or alongside the patient, and configured to axially advance, retract, and in some cases rotate and/or laterally deflect two or three or more different (e.g., concentrically or side by side oriented) intravascular devices. The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub can be in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device approximately or distally within the patient's vasculature.

The carriages on the drive table, which magnetically couple with the hubs to provide linear motion actuation, are universal. Functionality of the catheters/guidewire are provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
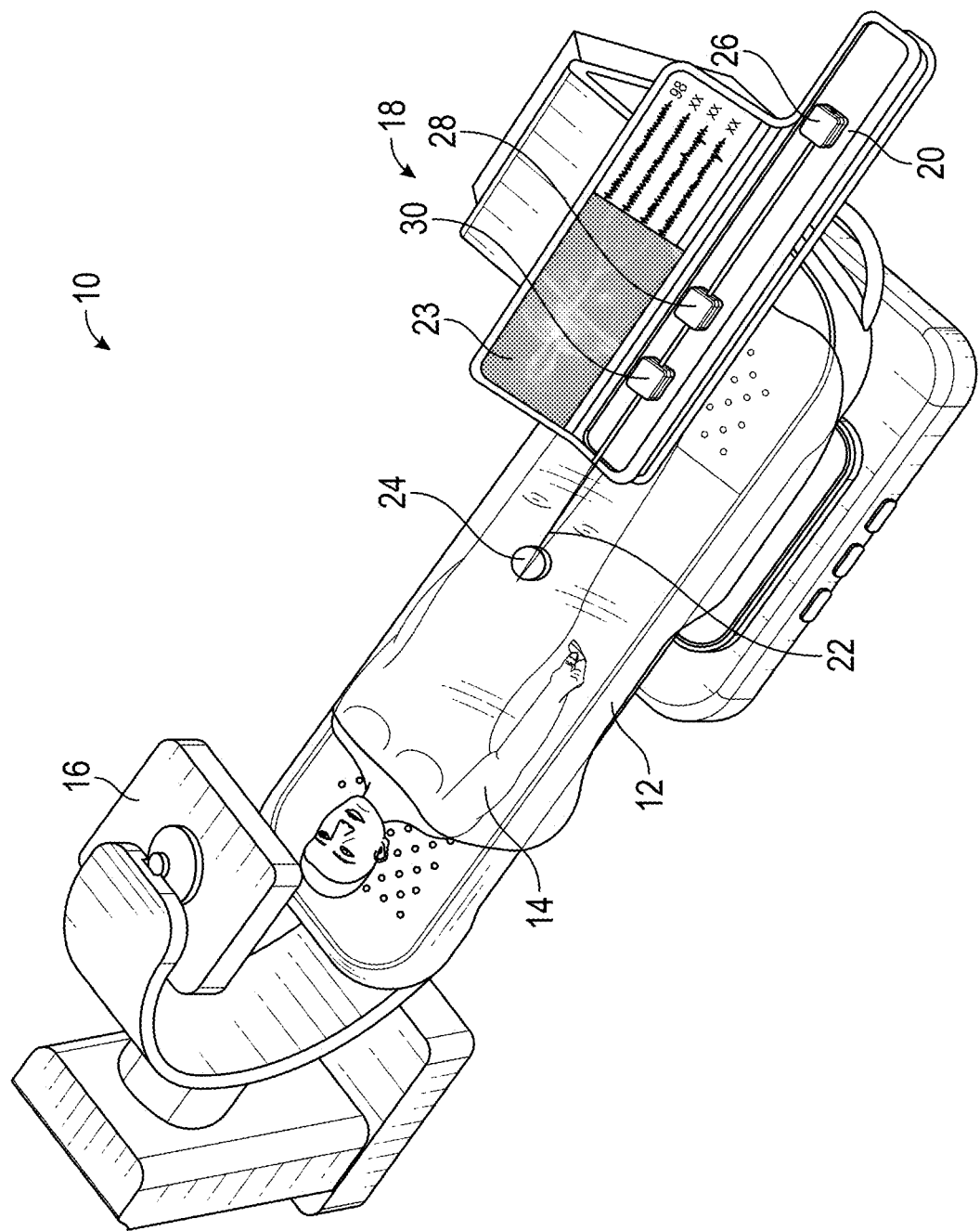
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, in intra-cardiac or structural heart applications, such as valve repair or replacement, or in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind .radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
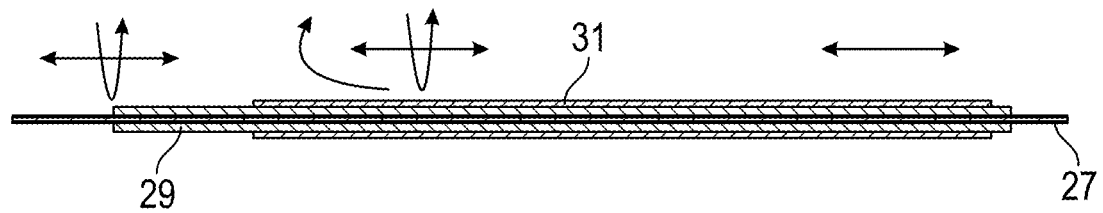
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
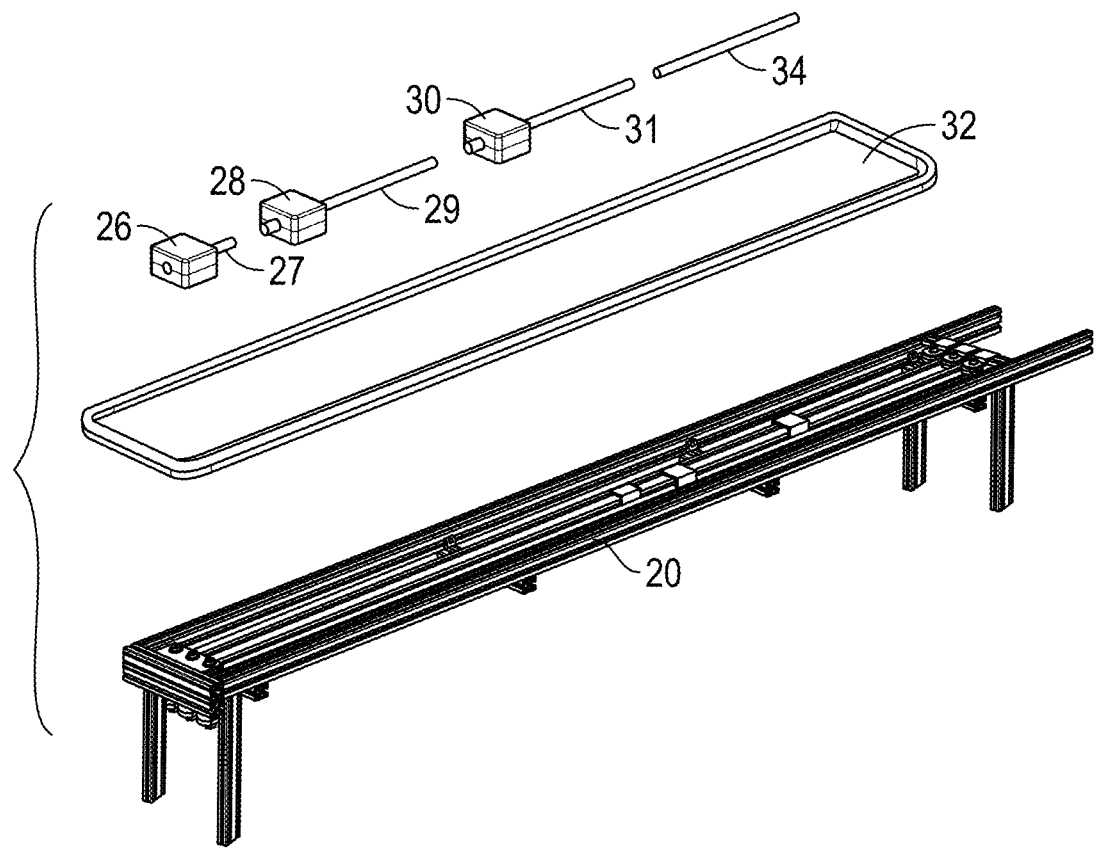
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti-buckling zone for resisting buckling of the portion of the interventional devices spanning the distance between the support table 20 and the femoral artery access point 24. The anti-buckling feature 34 may comprise a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be hollow and protect from abrasion, buckling, or damage at the inputs and outputs of the hubs. In some embodiments, the hollow extending element may be a hollow and flexible coating attached to a hub. The hollow, extending element (e.g., a hollow and flexible coating) may cover a portion of the device shaft when threaded through the hubs. In some embodiments in which the hollow extending element is a coating, the coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypotube, a spring, telescoping tubes, tensioned split tubing, or the like.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough.

The interventional device hubs may be separated from the support table 20 by sterile barrier 32. Sterile barrier 32 may comprise a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
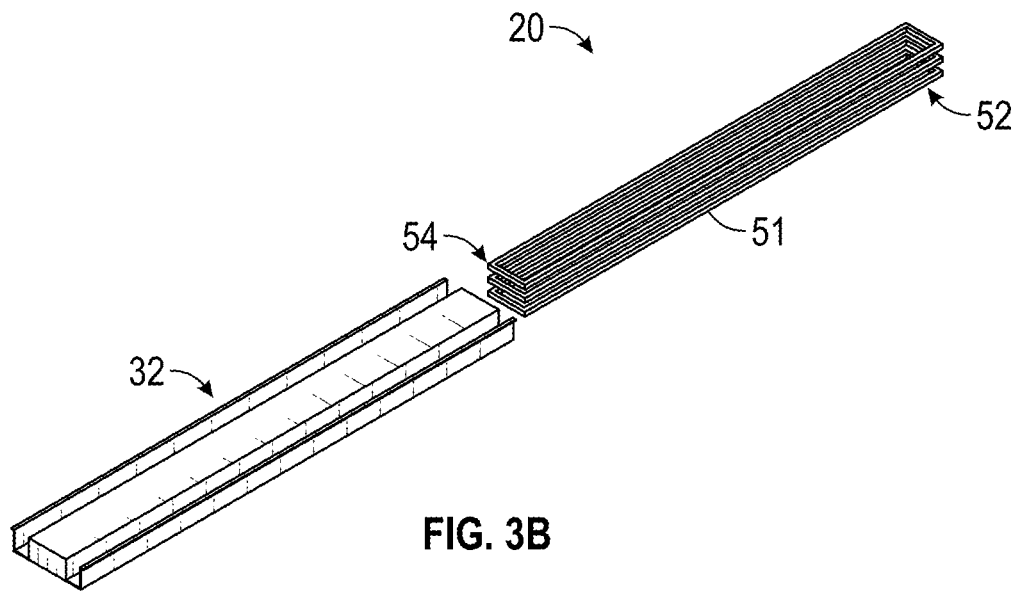
FIGS. 3B-3F show an alternate sterile barrier in the form of a shipping tray having one or more storage channels for carrying interventional devices.
Figure 3C:
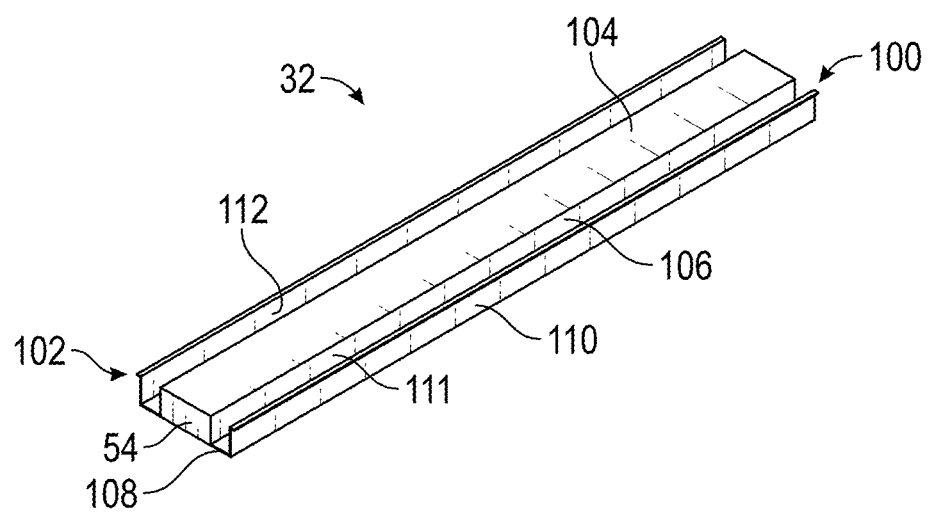

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figure 3D:
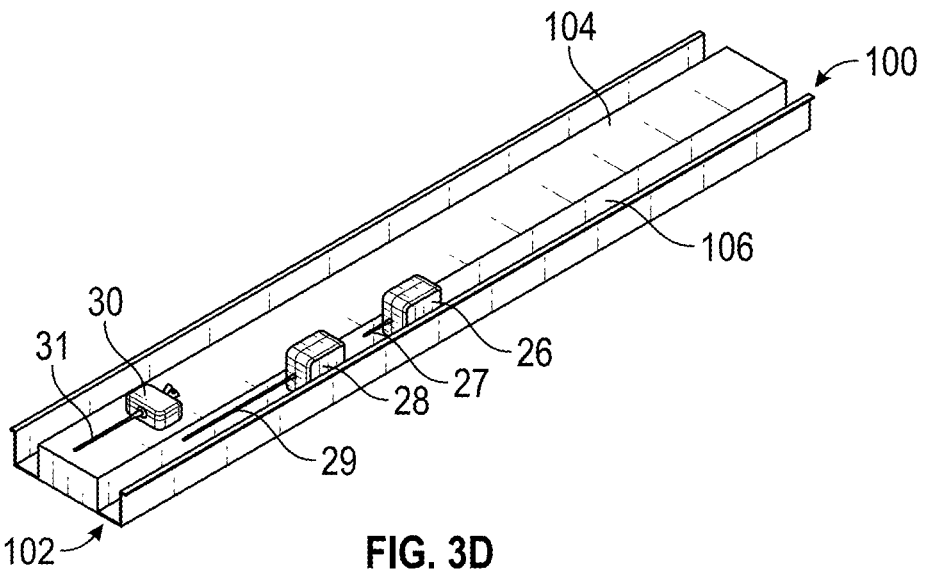

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
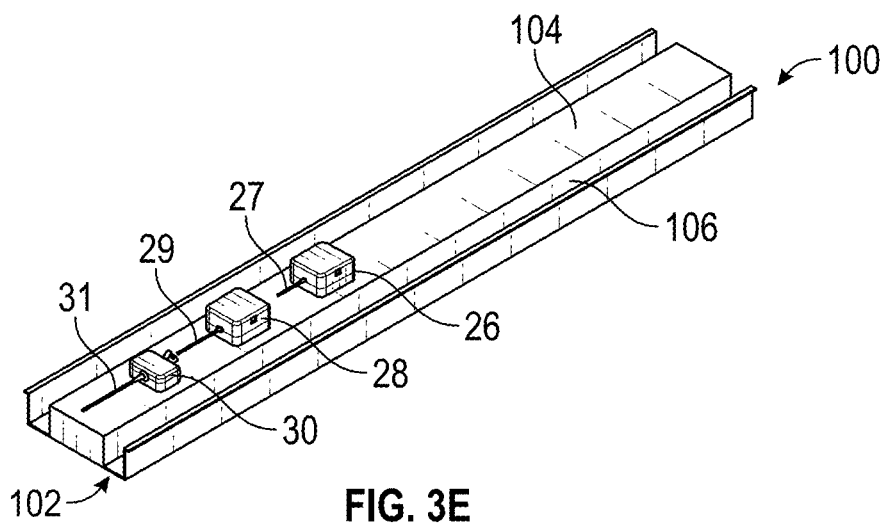
Figure 3F:
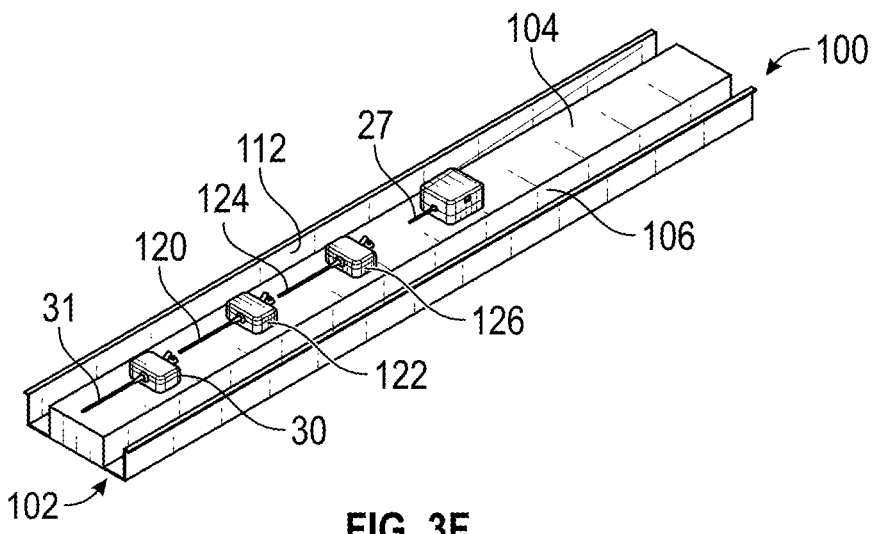

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. this may be accomplished in either a manual or a robotically driven procedure. In one example, the guide catheter 31 may comprise a catheter having an inner diameter of at least about 0.08 inches and in one implementation about 0.088 inches. The first procedure catheter 120 may comprise a catheter having an inner diameter within the range of from about 0.065 inches to about 0.075 inches and in one implementation catheter 120 has an inner diameter of about 0.071 inches. The second procedure catheter 124 may be an access catheter having an OD sized to permit advance through the first procedure catheter 120. The second procedure catheter maybe steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having a diameter of at least about 0.075 or at least about 0.080 inches in diameter. The catheter 120 may be an aspiration catheter having a diameter within the range of from about 0.060 to about 0.075 inches. The catheter 124 may be a steerable catheter with a deflectable distal tip, having a diameter within the range of from about 0.025 to about 0.050 inches. The guidewire 27 may have a diameter within the range of from about 0.014 to about 0.020 inches. In one example, the catheter 31 may have a diameter of about 0.088 inches, the catheter 120 about 0.071 inches, the catheter 124 about 0.035 inches, and the guidewire 27 may have a diameter of about 0.018 inches.

In one commercial execution, a preassembled access assembly (guide catheter, access catheter and guidewire)

may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

The trough 240 can include a drain hole 242. The trough 240 can be shaped, dimensioned, and/or otherwise configured so that fluid within the trough 240 empties to the drain hole 242. The drain hole 242 can include tubing, a barb fitting, and/or an on-off valve for removal of fluids from the trough 240. As shown in FIGS. 3I-3K, the trough 240 can be positioned at the proximal end of the sterile barrier 232. In alternate embodiments, the trough 240 may be positioned at a distal end of the sterile barrier 232. In some embodiments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dislodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alternate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as additional channels or wells may be provided, to hold additional medical devices or supplies that may be useful during the interventional procedure as well as to collect fluids and function as wash basins for catheters and related devices.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be in, about 15 in, between 13 in and 17 in, between 11 in and 19 in, or any other suitable width. A height $y_1$ of the support surface 204 can be 0.125 in, about 0.125 in, between 0.1 and in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle $\alpha$ of 90°, about 90°, between 80° and 100°, or any other suitable angle, and a radius of curvature of 0.125 in, about in, between 0.1 and 0.15 in, or any other suitable radius of curvature. In certain embodiments, an arc angle $\alpha$ of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height h1 of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configuration shown, for example, in FIGS. 3A-3F. For example, the support surface 104 can be positioned at about 90 degrees (or any other suitable angle) from a horizontal plane (e.g., rotated 90 degrees about a long axis of the support surface 104 relative to the embodiment shown in of FIGS. 3A-3F). A vertical configuration may provide for easier interaction with the drive system 18 by a physician, A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figure 4:
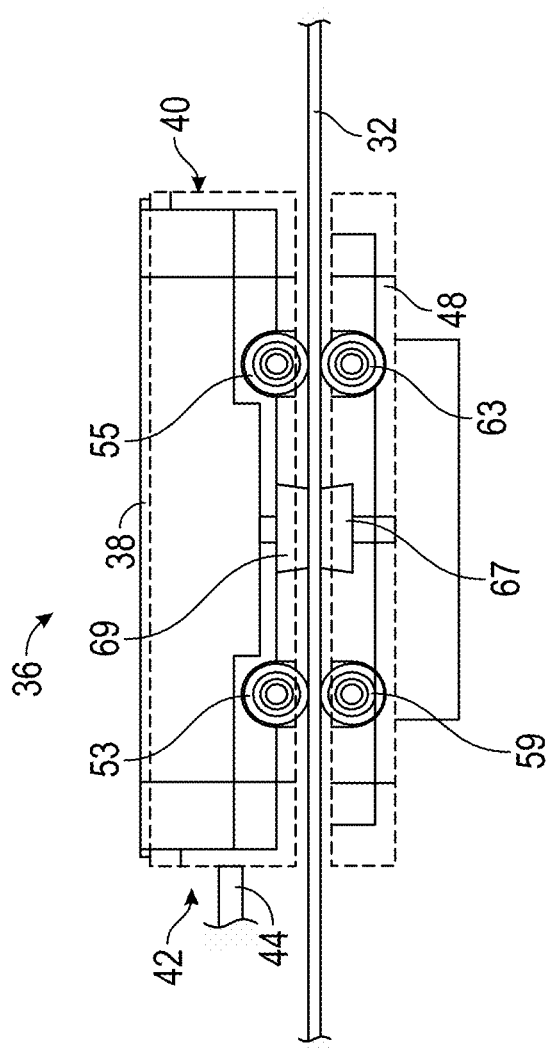
FIG. 4 is a schematic elevational cross section through a hub adapter having a drive magnet separated from an interventional device hub and driven magnet by a sterile barrier.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field. Movement of the hub adapter is driven by a drive system carried by the support table and described in additional detail below.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some implementations, the space is within the range of from about 0.03 centimeters (about 0.010 inches) and about 0.041 centimeters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 centimeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
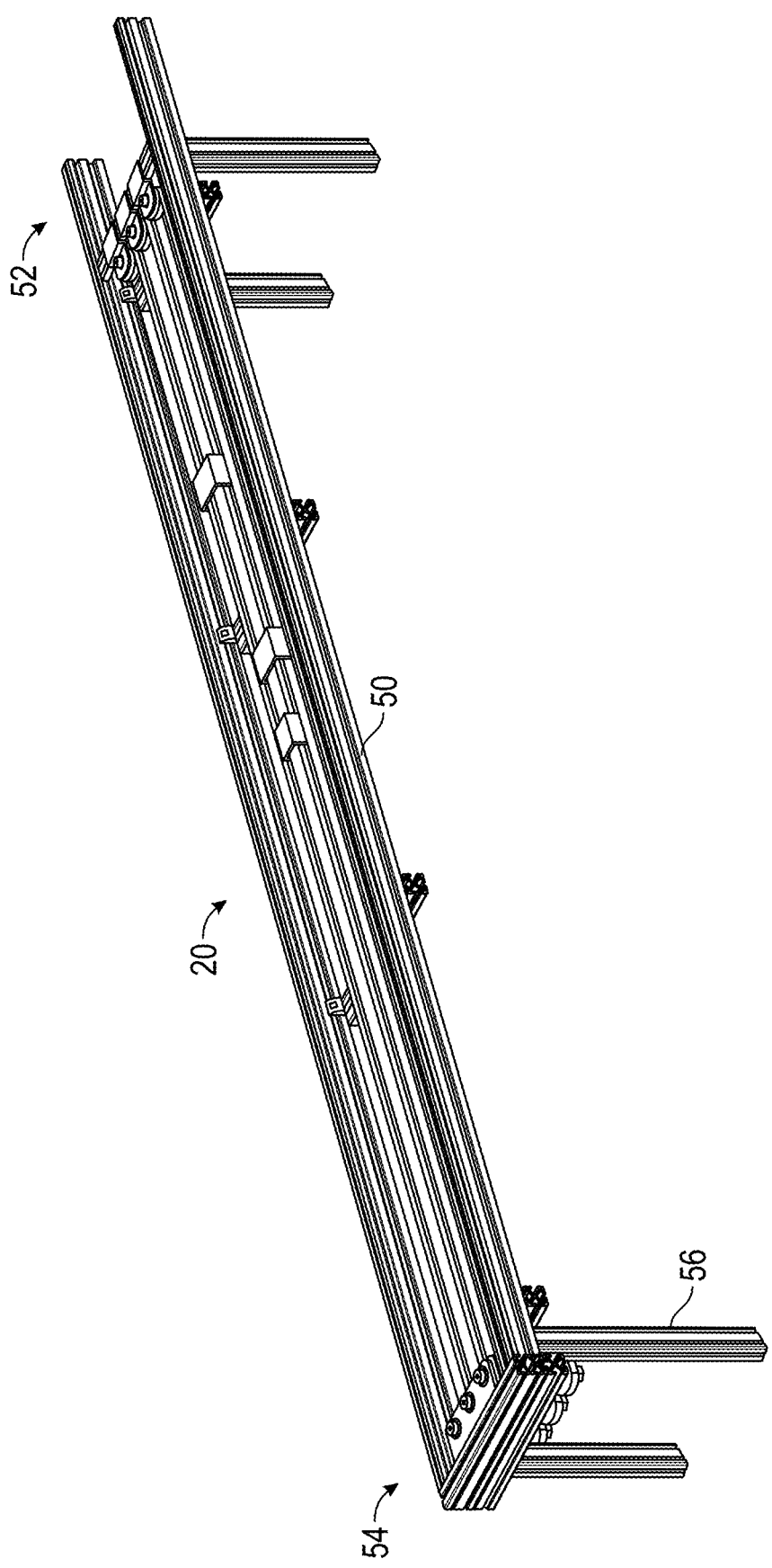
FIG. 6 is a perspective view of a support table.

Referring to FIG. 6, there is schematically illustrated one example of a low-profile linear drive support table 20. Support table 20 comprises an elongated frame 51 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 51 over or adjacent to the patient.

Figure 7:
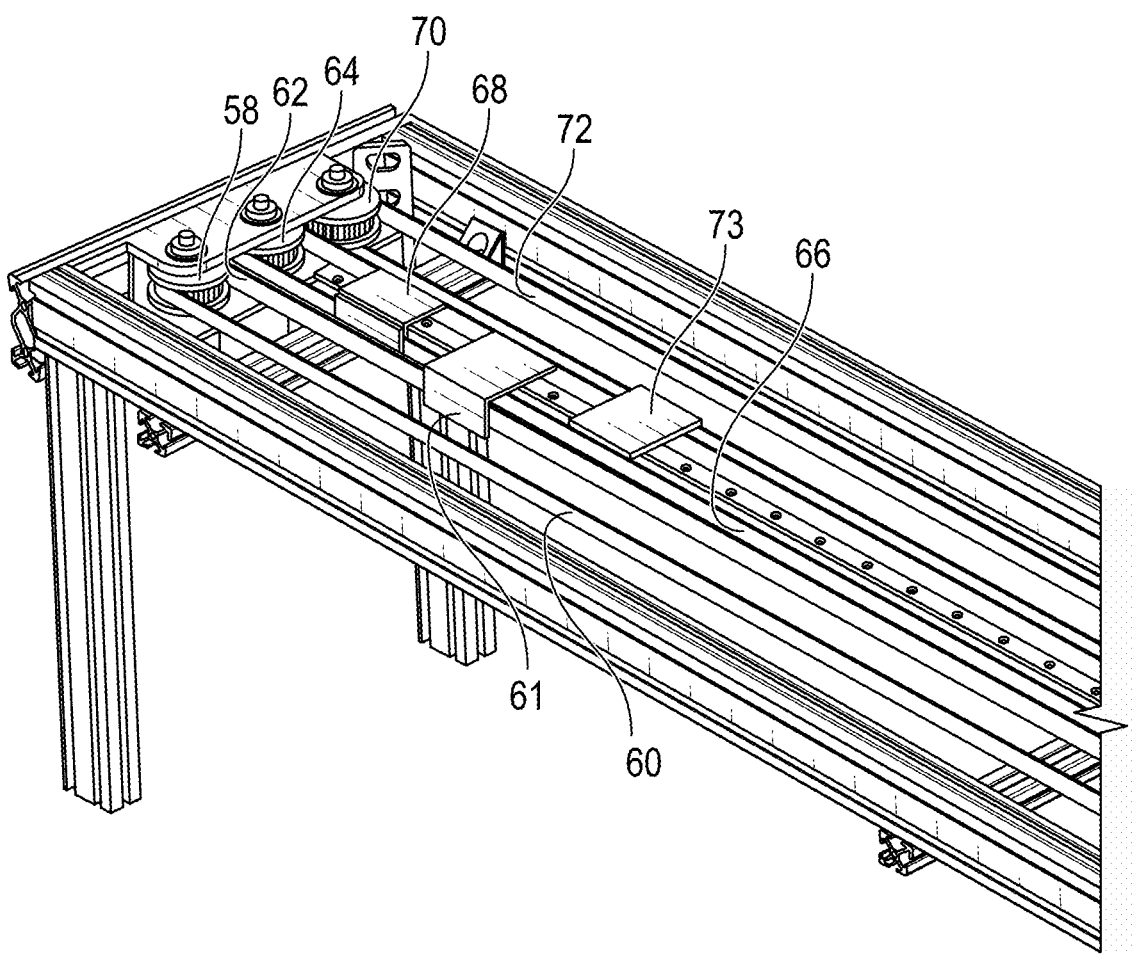
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
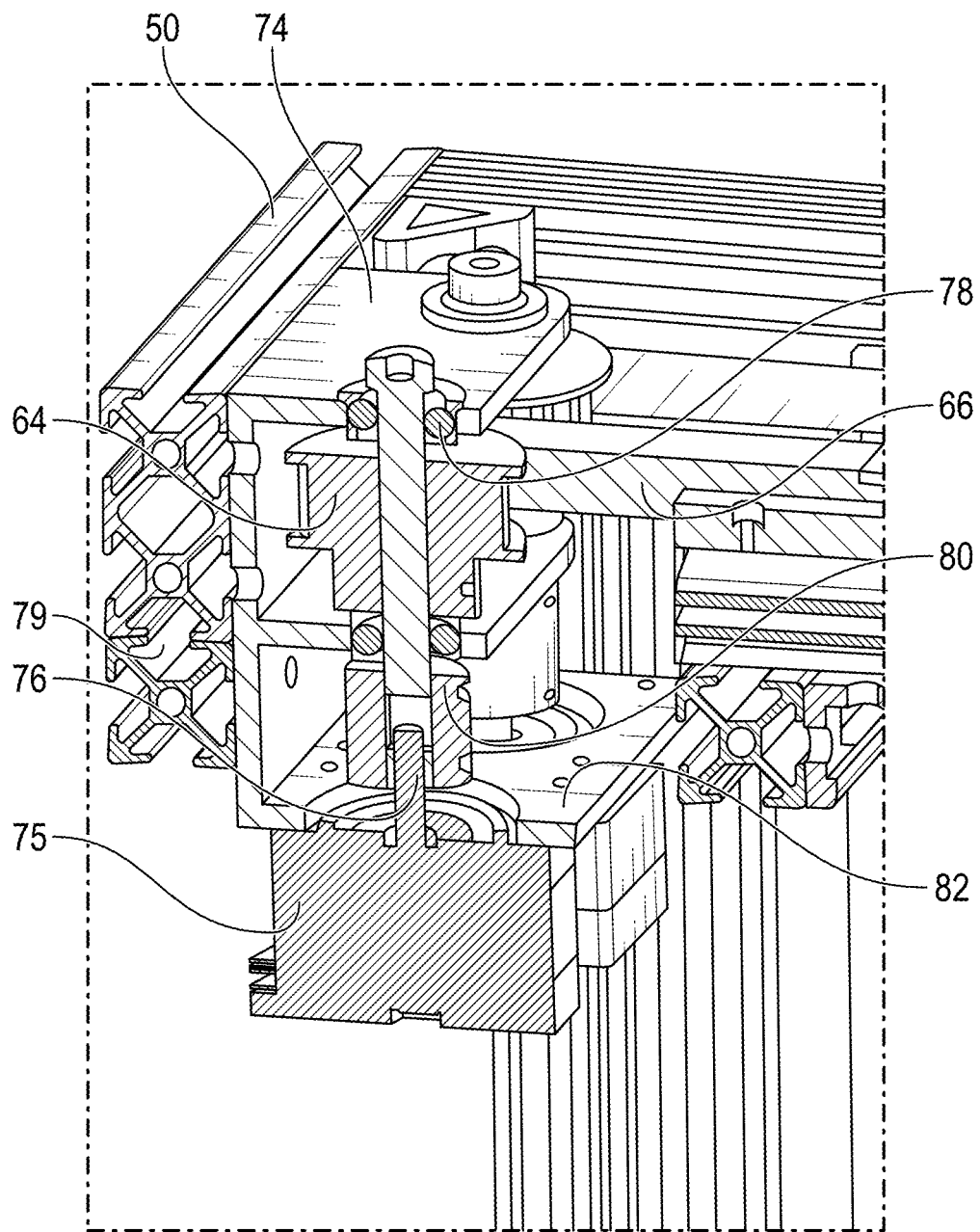
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 maybe similarly constructed and are not further detailed herein. In some embodiments, the drive systems described herein may be a rack and pinion drive table system that is foldable. In such embodiments, motors 75 may be attached to and move with the carriages.

Figure 9:
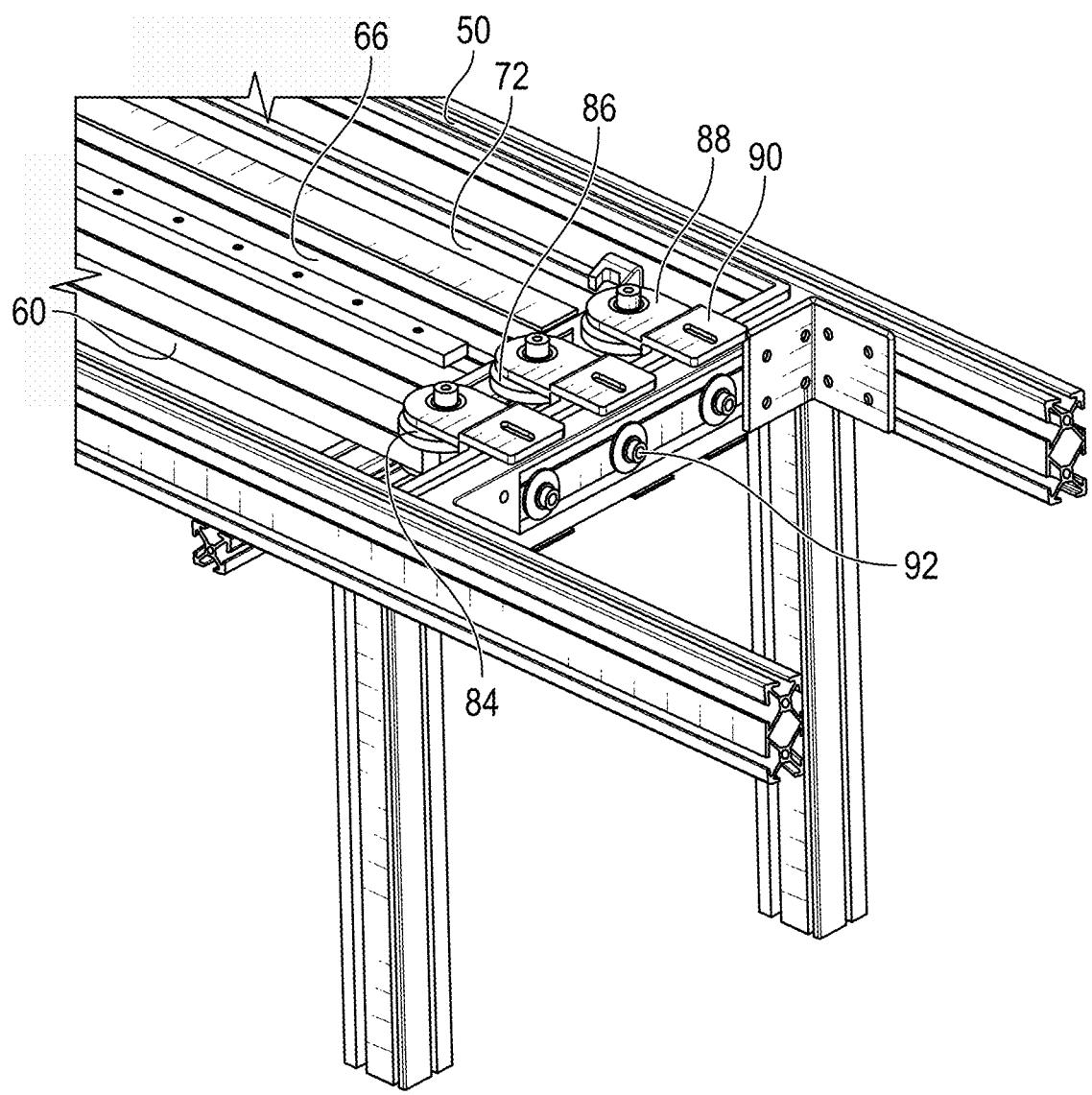
FIG. 9 is a close-up view of a pulley end of the support table.
Figure 10:
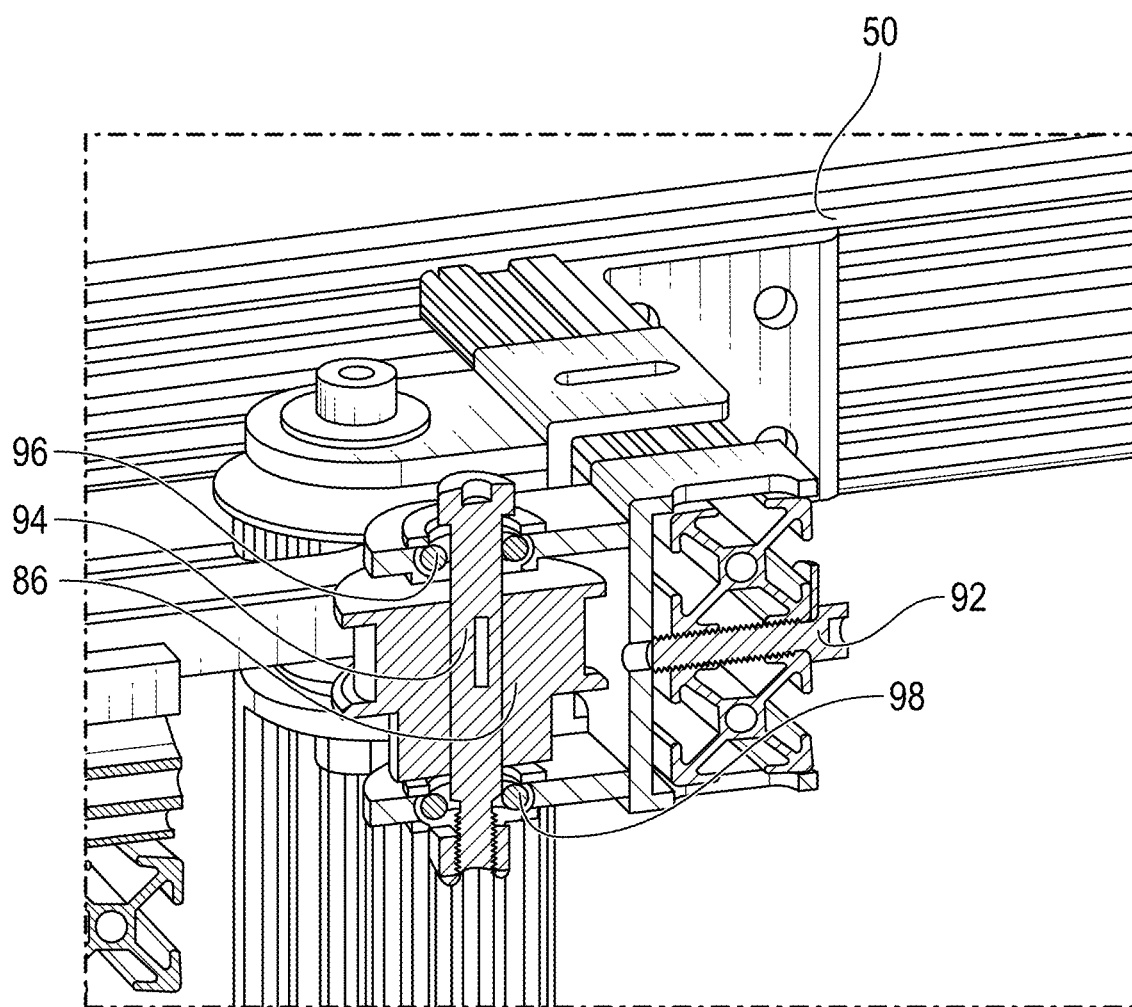
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 5A:
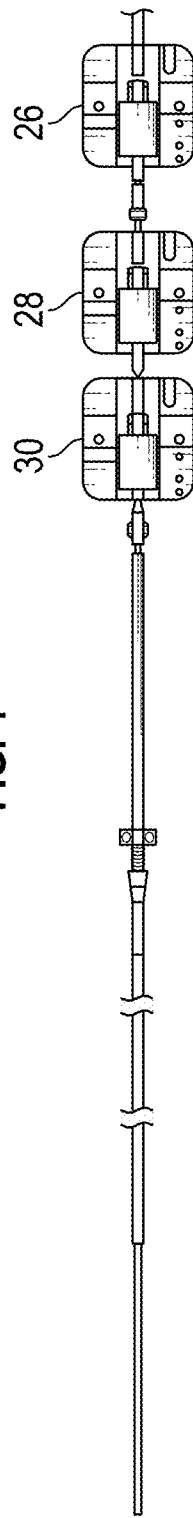
FIGS. 5A and 5B schematically illustrate a three interventional device and a four interventional device assembly.
Figure 5B:
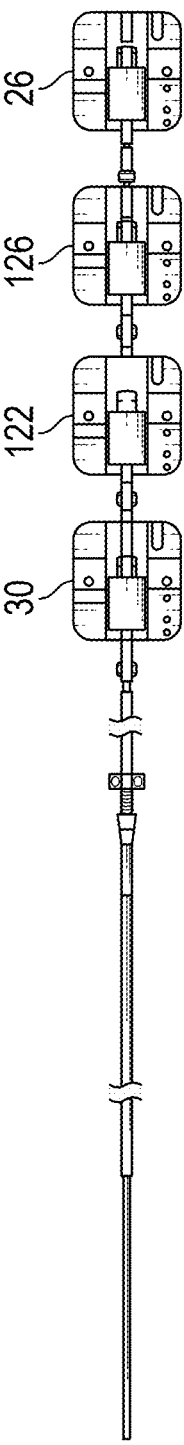
Figure 11:
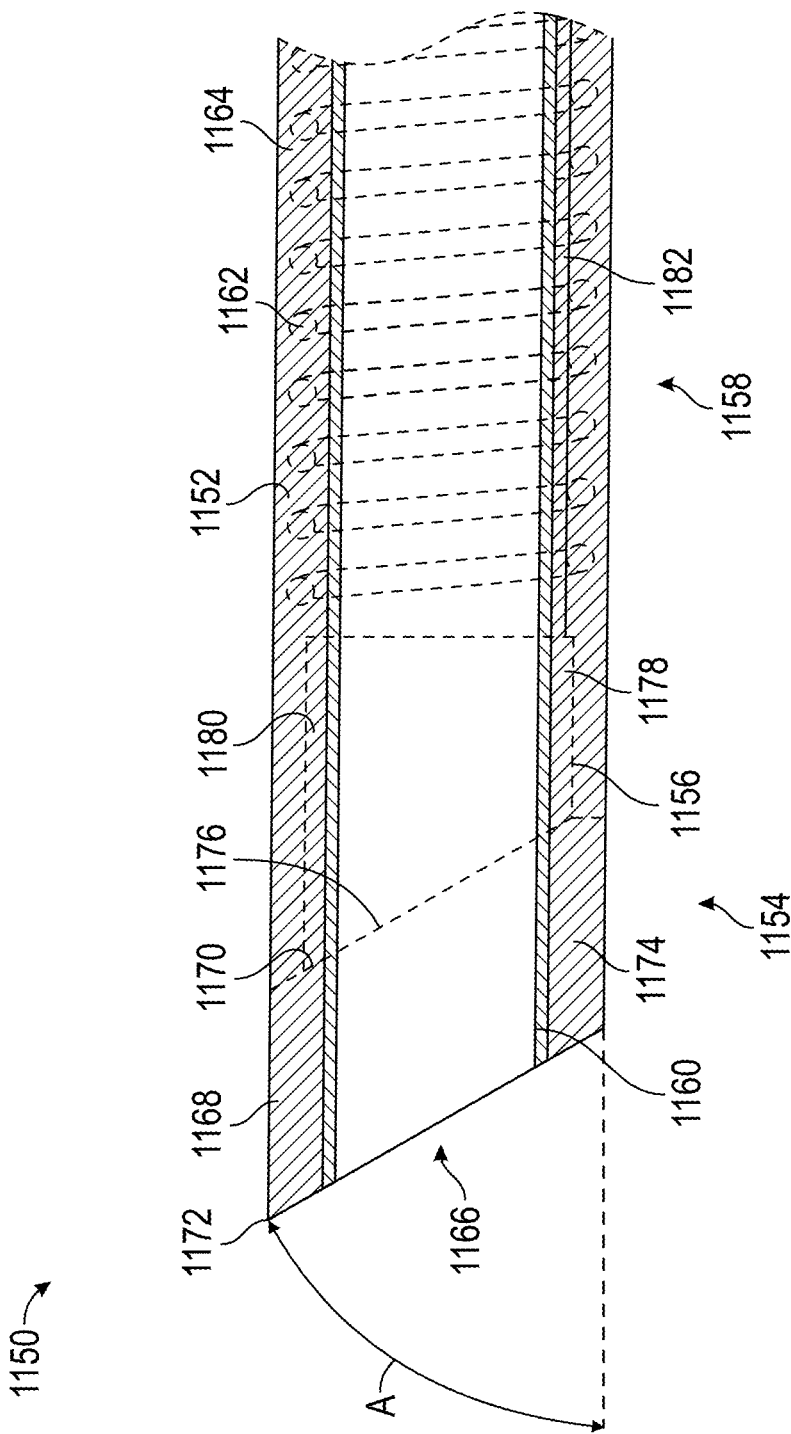
FIG. 11 is a side elevational cross-section through a distal portion of a catheter such as any of those shown in FIGS. 5A and 5B.

Any of the catheters illustrated, for example, in FIG. 5A, 5B or 11 generally comprise an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 comprises a tubular body 1152 which includes an advance segment 1154, a marker band 1156 and a proximal segment 1158. An inner tubular liner 1160 may extend throughout the length of the distal catheter tip 1150, and may comprise dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may comprise a distal extension of the outer tubular jacket 1164 and optionally the inner liner 1160, without other internal supporting structures distally of the marker band 1156. Outer jacket 1164 may comprise extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may comprise materials such as Vectran®, Kevlar®, Polyester®, Spectra®, Dyneema®, Meta-Para-Aramide®, or any combinations thereof. At least one of the one or more tension element 1182 may comprise a single fiber or a multi-fiber bundle, and the fiber or bundle may have a round or rectangular (e.g., ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
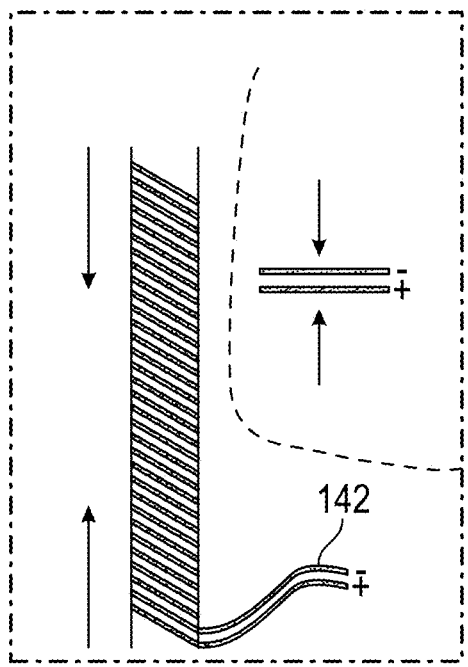
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
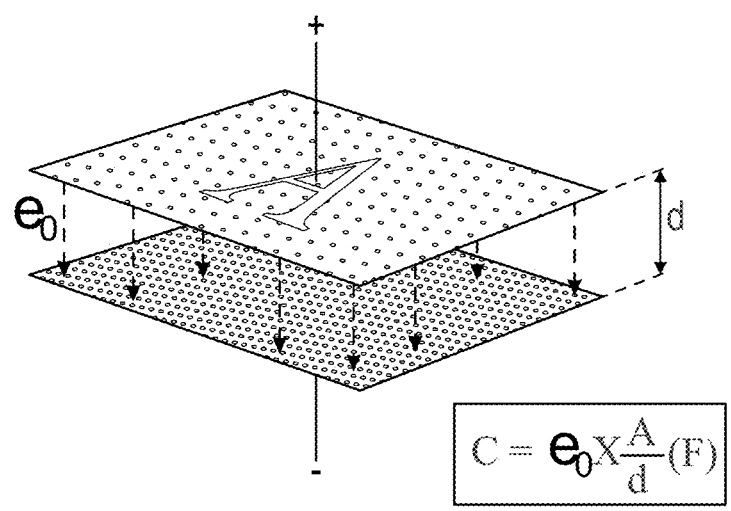

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
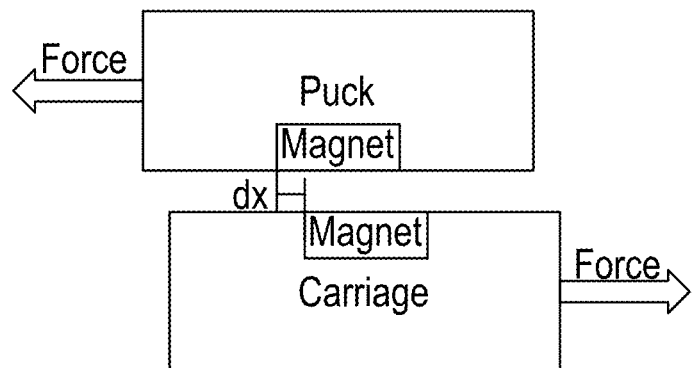
FIGS. 13A and 13B schematically illustrate a sensor for measuring elastic forces at the magnetic coupling between the hub and corresponding carriage.
Figure 13B:
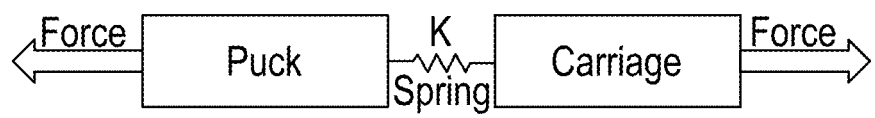

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the puck and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the pucks through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
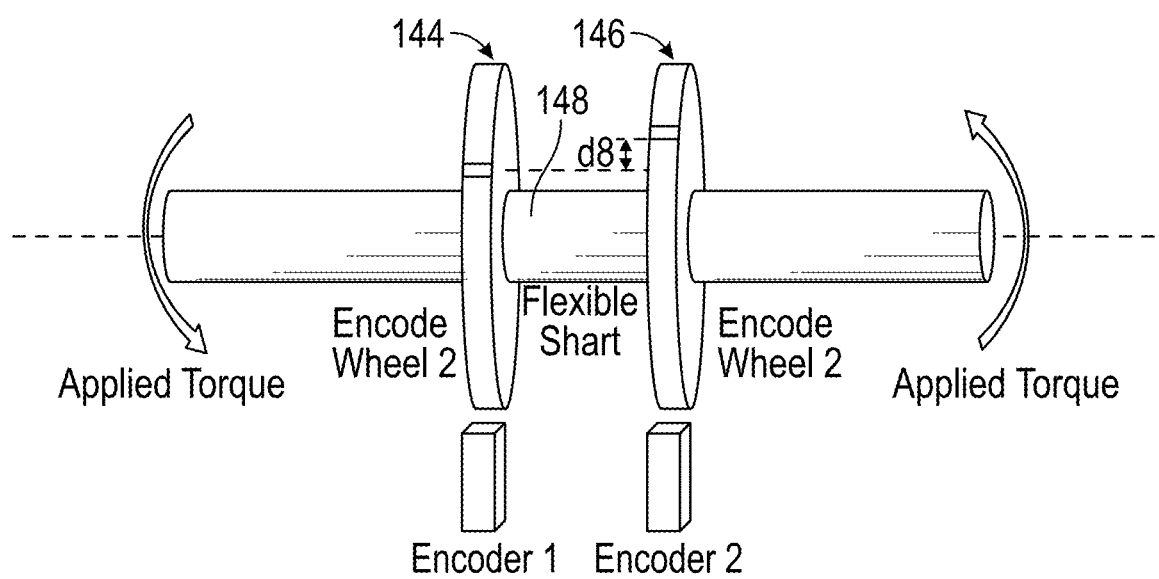
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders (dθ) tells us the torque. T=k*dθ, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
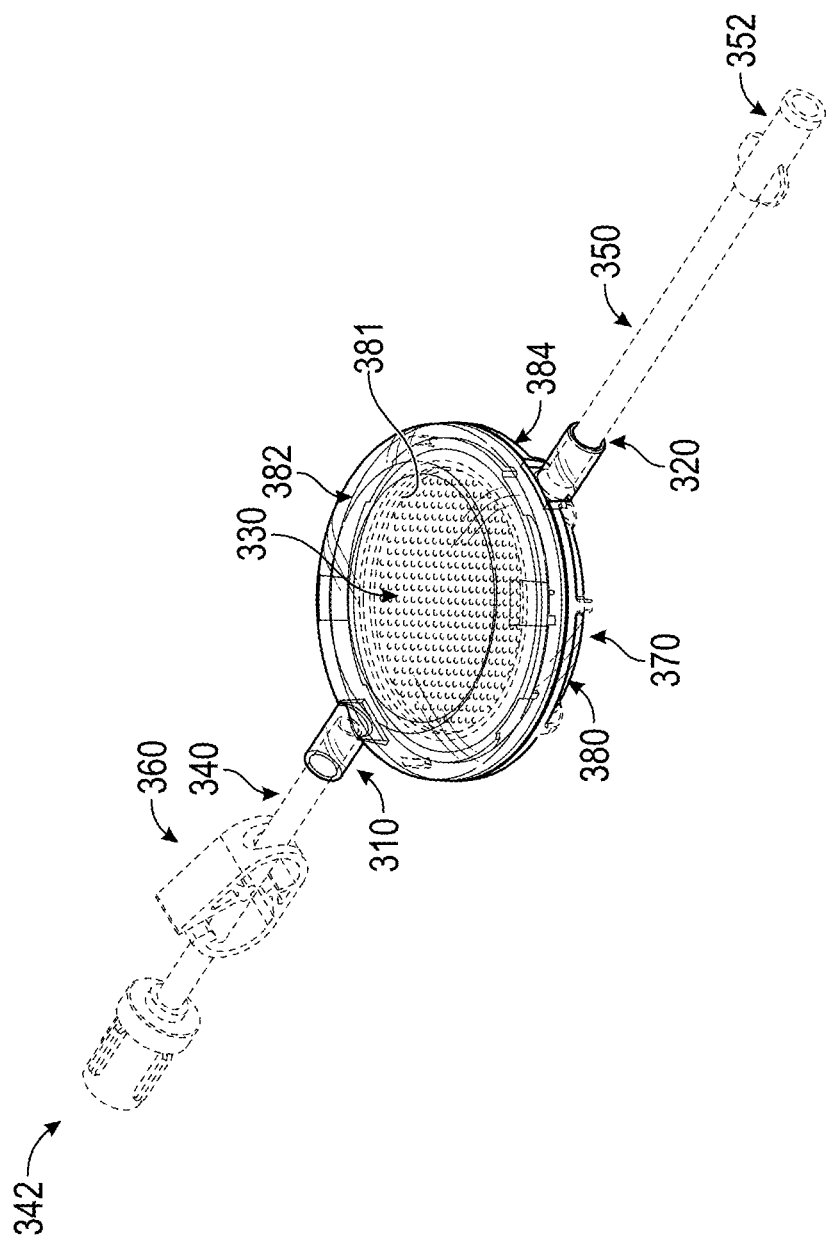
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp 360. The clamp 360 can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

Figure 16A:
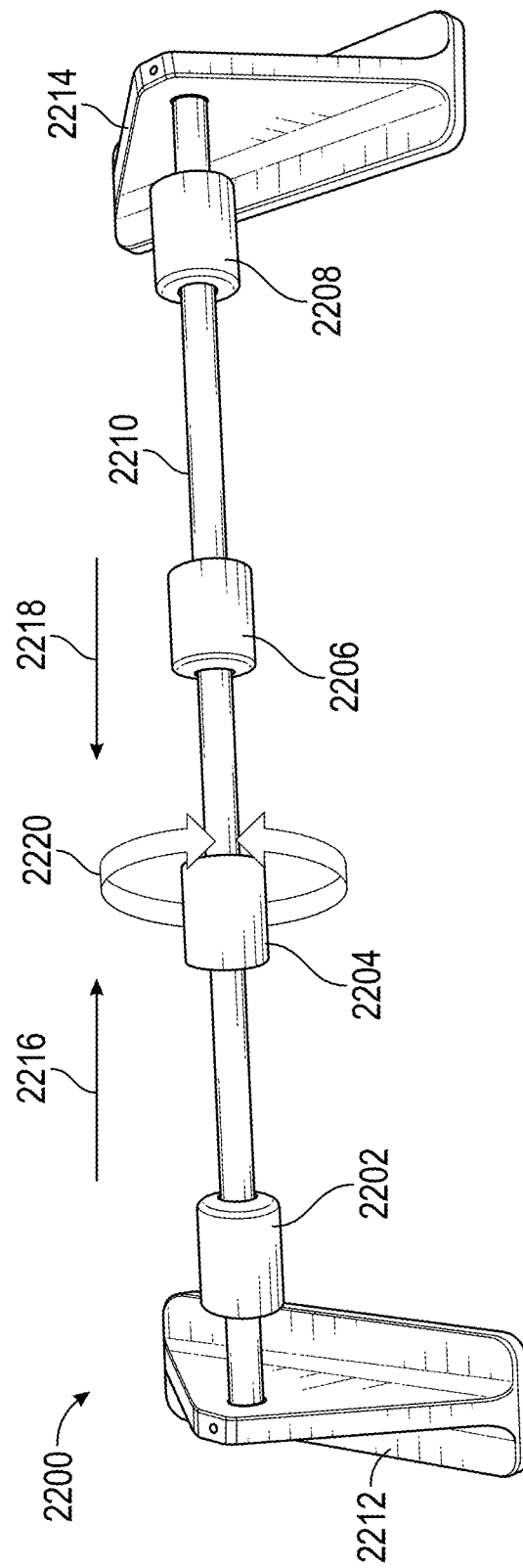
FIGS. 16A-16C illustrate an example control mechanism for manipulating interventional devices driven by respective hubs.
Figure 16B:
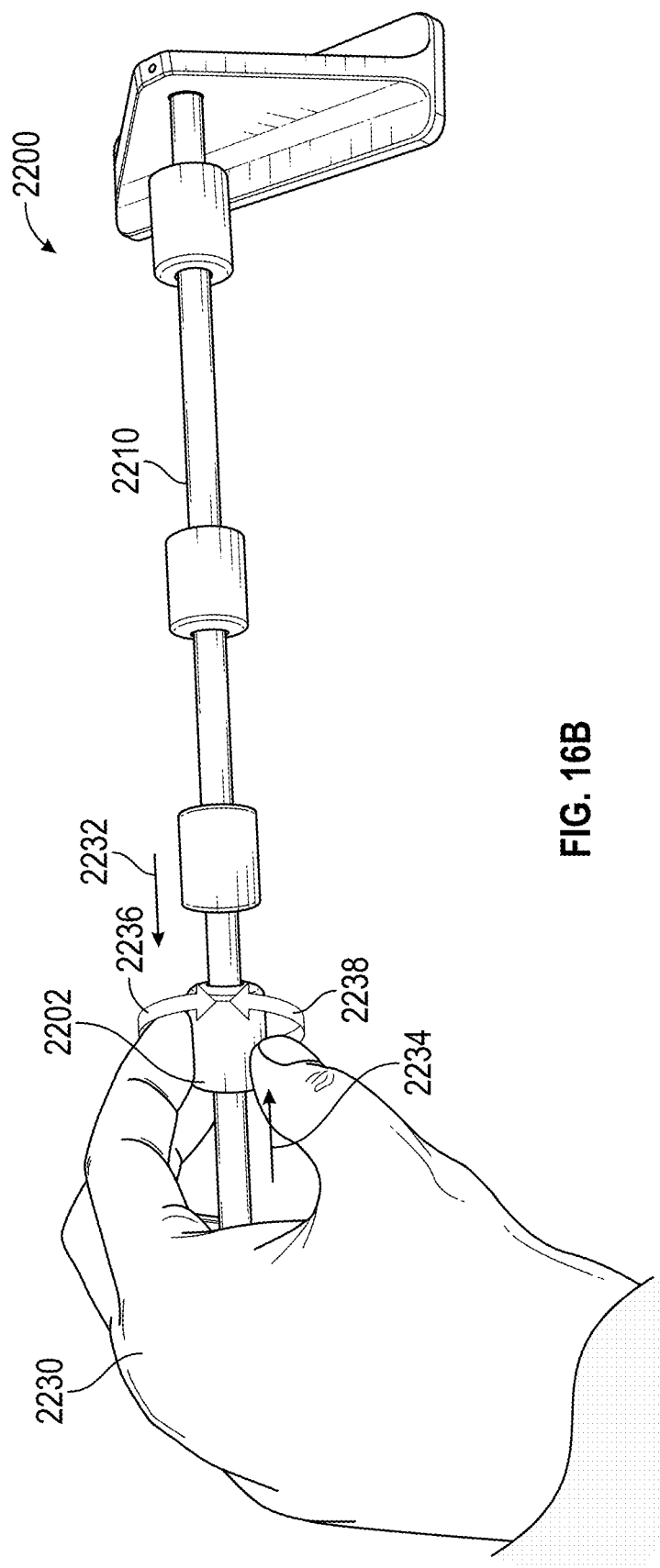
Figure 16C:
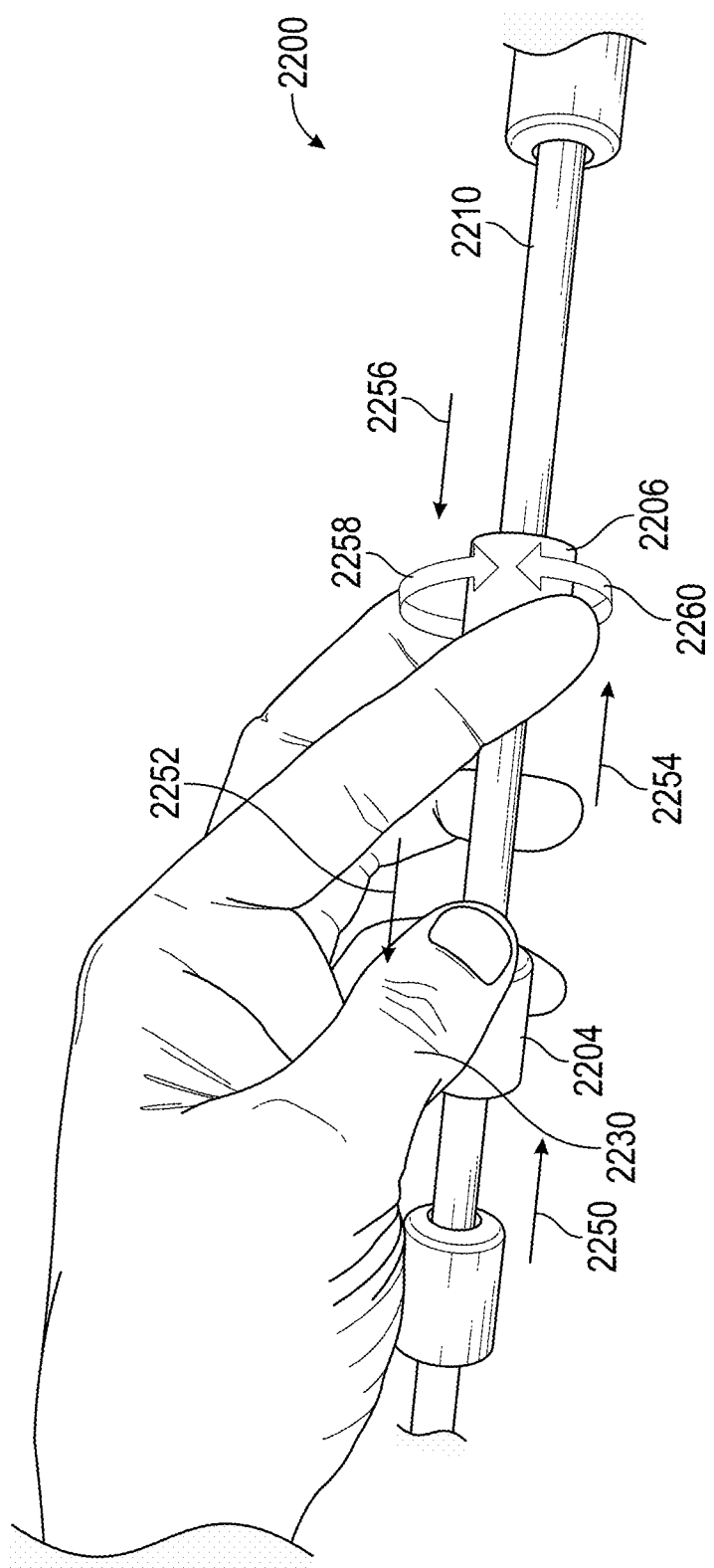

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 include a first control 2202, a second control 2204, a third control 2206, and a fourth control 2208. More or fewer controls may be provided, depending upon the intended interventional devices configuration. Each control 2202-2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device.

Axial movement of a control may be configured to move the coupled hub on a 1:1 basis, or on a non 1:1 scaled basis. For example, if the user 2230 advances the control 2022 about 5 millimeters distally along the shaft 2210, then the corresponding hub may responsively move 5 millimeters in the distal direction.

If the user 2230 rotates the control 2022 about its rotational axis by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using controls 2202-2208. For example, controls 2202-2208 may be configured to drive a shape change and/or stiffness change of a corresponding interventional device. Controls 2202-2208 may be toggled between different operating modes. For example, controls 2202-2208 may be toggled between movement driven by acceleration and velocity to movement that reflects actual linear displacement or rotation.

In some implementations, the control mechanism 2200 may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism 2200 may include haptic components to provide haptic feedback to a user operating the controls. For example, if the control 2202 is triggering movement of a catheter and the catheter detects a large force at the tip, the control 2202 may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
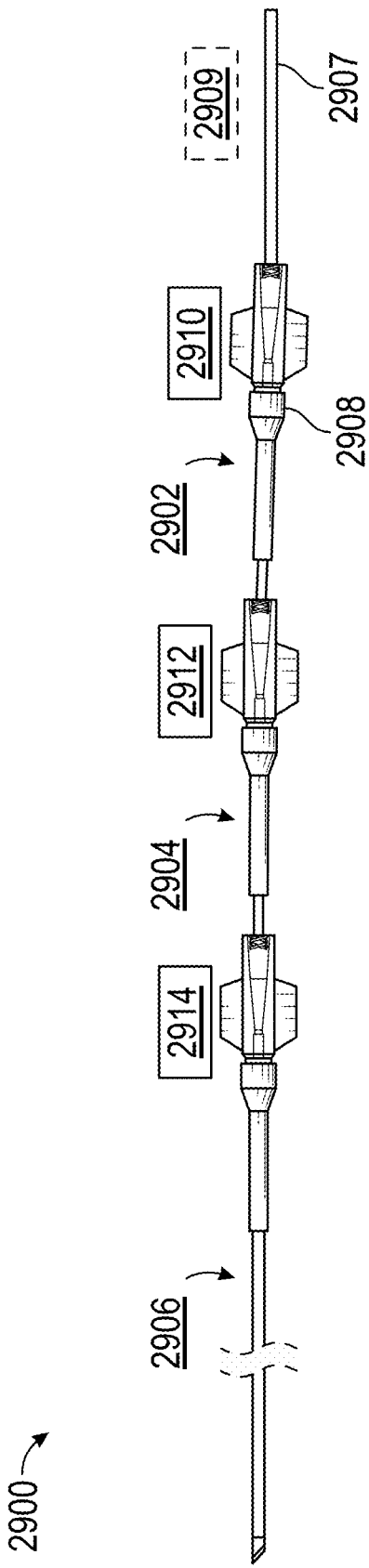
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more catheters of assembly 2900.

In operation, the multi-catheter assembly 2900 may be used without having to exchange hub components. For example, in the two stage procedure disclosed previously, a first stage for achieving supra-aortic access, includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. Additional details regarding hemostasis valves are included in U.S. patent application Ser. No. 17/879,614, entitled Multi Catheter System With Integrated Fluidics Management, filed Aug. 2, 2022, which is hereby expressly incorporated in its entirety herein Once access above the aortic arch has been achieved, the insert or access catheter 2902 (associated with insert catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the catheter 2906 may function as a guide catheter. The catheter 2904 may function as a procedure (e.g., aspiration) catheter. In some embodiments, the catheter 2906 may function to perform aspiration in addition to functioning as a guide catheter, either instead of or in addition to the catheter 2904. The access catheter 2902 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having a diameter of at least about 0.075 or at least about 0.080 inches in diameter. The procedure catheter 2904 may be an aspiration catheter having a diameter within the range of from about to about 0.075 inches. The access catheter 124 may be a steerable catheter with a deflectable distal tip, having a diameter within the range of from about 0.025 to about 0.050 inches. The guidewire 2907 may have a diameter within the range of from about 0.014 to about 0.020 inches. In one example, the guide catheter 2906 may have a diameter of about inches, the procedure catheter 2904 about 0.071 inches, the access catheter 2902 about inches, and the guidewire 2907 may have a diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Referring to FIG. 18A, the three catheter interventional device assembly 2900 is shown driven through an introducer sheath 3002, up through the iliac artery 3004 and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced up to the petrous segment 3018 of the internal carotid artery 3016.

Figure 18E:
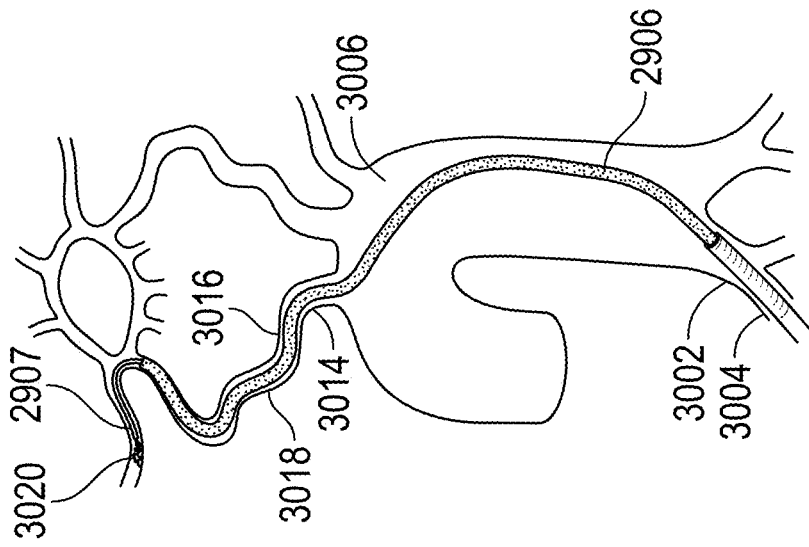
Figure 18D:
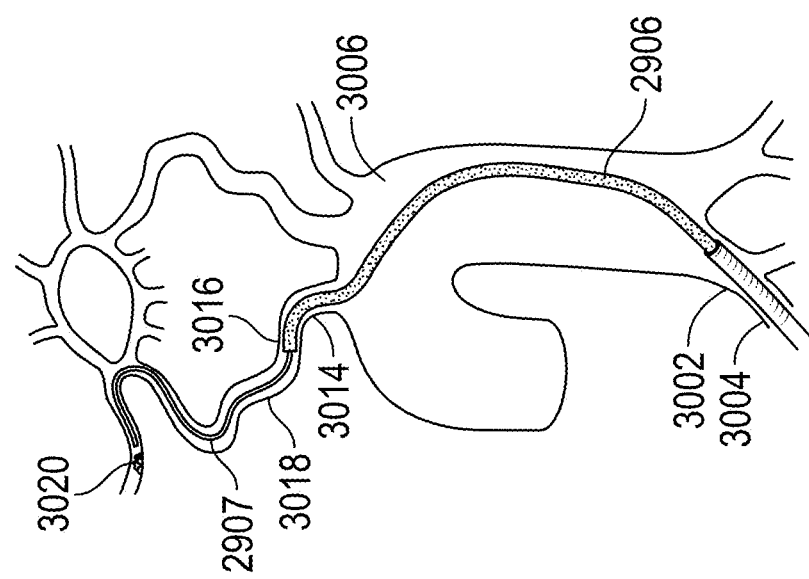

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the M1 segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub 2909 on the guidewire 2907 to a first drive magnet, magnetically coupling a second hub 2910 on the access catheter 2902 to a second drive magnet, magnetically coupling a third hub 2912 on the procedure catheter 2904 to a third drive magnet, and magnetically coupling a fourth hub 2914 on the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

An example robotic control system may include at least a guidewire hub (e.g., guidewire hub 2909) configured to adjust each of an axial position and a rotational position of a guidewire 2907. The robotic control system may also include an access catheter hub 2910 configured to adjust axial and rotational movement of an access catheter 2902. The robotic control system may also include a guide catheter hub 2914 configured to control axial movement of a guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The access catheter hub 2910 is configured to couple to an access catheter hub adapter by magnetically coupling the access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail in FIG. 4 above.

In some embodiments, the robotic control system includes a second driven magnet on the access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the access catheter hub 2910, the procedure catheter hub 2912, and/or the guide catheter hub 2914) with one or more drive mechanisms.

Figure 19:
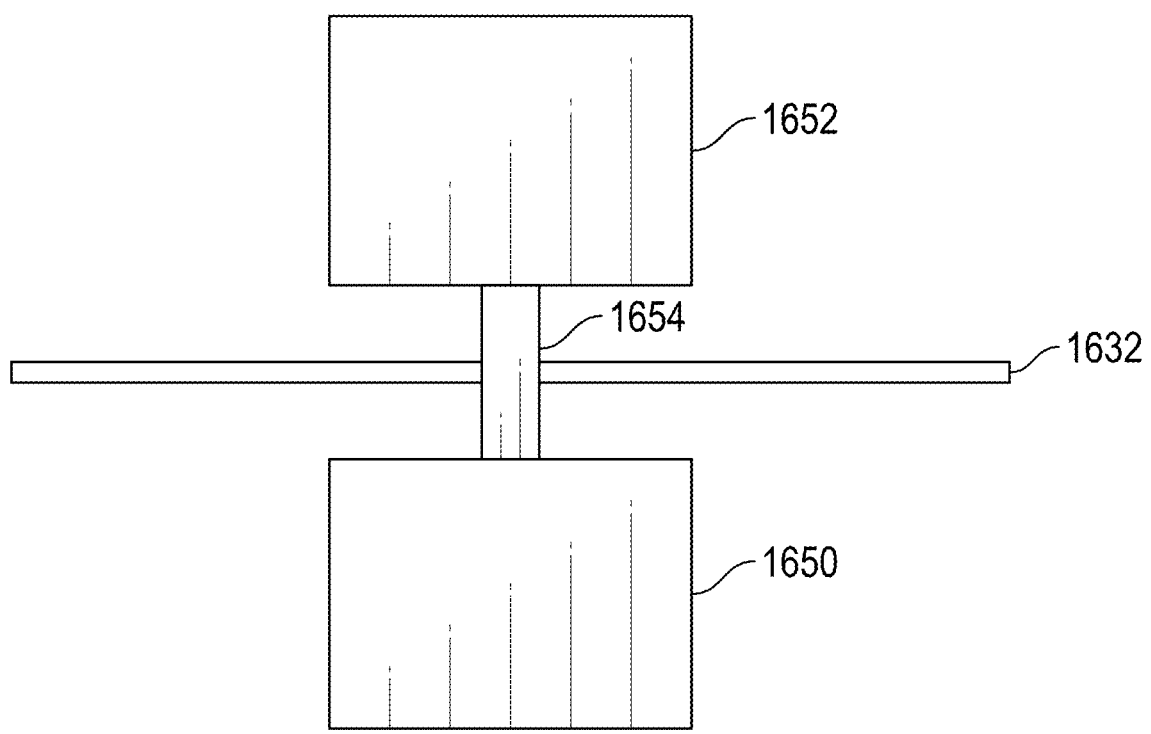
FIG. 19 schematically illustrates an embodiment of a mechanical coupling between a drive mechanism and a driven mechanism.

FIG. 19 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the access catheter hub 2910, the procedure catheter hub 2912, or the guide catheter hub 2914). In some instances, the mechanical coupling mechanism 1654 may comprise a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may comprise a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the copative edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The mechanical coupling 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn the sterile pulley in the hub via the sterile splined shaft.

It will be understood by one having skill in the art that any embodiment as described herein may be modified to incorporate a mechanical coupling mechanism, for example, as shown in FIG. 19.

The interventional devices described herein may be provided individually or at least some of the interventional devices can be provided in a preassembled (e.g., nested or stacked) configuration. For example, the interventional devices may be provided in the form of an interventional device assembly, such as interventional device assembly 2900, in a concentric nested or stacked configuration. If provided individually, each catheter (and in some embodiments, each corresponding catheter hub) can be unpackaged and primed to remove air from its inner lumen, for example, by flushing the catheter (and in some embodiments, the corresponding catheter hub) to remove air by displacing it with a fluid, such as saline. After priming, the interventional devices can be manually assembled into a stacked configuration so that they are ready for introduction into the body for a surgical procedure, for example, via an introducer sheath.

Assembling the devices into a stacked configuration can include individually inserting interventional devices into one another by order of size. For example, an interventional device having a second largest diameter can be inserted into the lumen of an interventional device having a largest diameter. An interventional device having a third largest diameter can then be inserted into the interventional device having the second largest diameter and so on.

For example, with respect to FIG. 17, assembly can be performed by first inserting a distal end of the catheter 2904 through the hub 2914 and into the catheter 2906. The catheter 2904 can be advanced through the catheter 2906 until the distal tip of the catheter 2904 is flush with or extends beyond the distal tip of the catheter 2906. Then, the distal end of the catheter 2902 can be inserted through the hub 2912 and into the catheter 2904. The catheter 2902 can be advanced through the catheter 2904 until the distal tip of the catheter 2902 is flush with or extends beyond the distal tip of the catheter 2904. Then, the distal end of the guidewire 2907 can be inserted through the hub 2910 and into the catheter 2902. The guidewire 2907 can be advanced through the catheter 2902 until the distal tip of the guidewire 2907 is flush with or extends beyond the distal tip of the catheter 2902.

Embodiments in which two or more of the interventional devices are packaged together as a single unit in an assembled (e.g., nested or stacked) configuration may provide efficient unpackaging prior to use and efficient assembly within a robotic control system. The interventional devices may be pre-mounted to their respective hubs prior to packaging. In certain embodiments, two or three or more interventional devices may be packaged in a fully nested (i.e., fully axially inserted) configuration or nearly fully nested configuration. In a fully nested configuration, each interventional device is inserted as far as possible into an adjacent distal hub and interventional device. Such a fully nested configuration may minimize a total length of the interventional device assembly and minimize the size of the packaging required to house the interventional device assembly.

The interventional devices may also be sterilized prior to packaging while in the assembled configuration, for example, using ethylene oxide gas. For interventional devices in a nested or stacked configuration, ethylene oxide gas can be provided in a space between adjacent interventional devices (for example, an annular lumen between an outer diameter of a first interventional device nested within a second interventional device and the inner diameter of the second interventional device) for sterilization. In some embodiments, the interventional device assembly can be packaged in a thermoformed tray and sealed with an HDPE (e.g., Tyvek®) lid. The interventional device assembly can be unpackaged by removal (e.g., opening or peeling off) of the lid by a user in a non-sterile field. A user in the sterile field can then remove the interventional device assembly and place it on the sterile work surface, for example, of a robotic drive table, as described herein.

Packaging the interventional devices in an assembled configuration and sterilized state can reduce the time associated with unpackaging and assembly of individual interventional devices and facilitate efficient connection to a robotic drive system. Each interventional device and hub combination may further be packaged with a fluidics connection for coupling to a fluid source and/or a vacuum source. In some embodiments, each hub or a hemostasis valve coupled to the hub may include the fluidics connection.

After the interventional device assembly is unpackaged (e.g., after the interventional device assembly is positioned on the robotic drive table), priming can be performed while the devices are concentrically nested or stacked. This is preferably accomplished in each fluid lumen, such as, for example, the annular lumen between the catheter 2906 and the catheter 2904 and in between each of the additional concentric interventional devices in the concentric stack. In certain embodiments, the fluid lumen can include a lumen between a distal hub and a proximal interventional device, such as, for example, the lumen between the hub 2914 and the catheter 2904.

The fluidics connections can be connected to a fluidics system for delivering saline and contrast media to the catheters and providing aspiration. In some embodiments, the fluidics connections may be passed outside the sterile field for connection to the fluidics system. Once connected, the fluidics system can perform a priming sequence to flush each catheter of the interventional device assembly with saline. The priming sequence may also include flushing each corresponding catheter hub with saline. The saline may be de-aired or de-gassed by the fluidics system prior to priming. In some embodiments, a vacuum source of the fluidics system can also be used to evacuate air from each catheter while flushing with saline. In certain embodiments, a tip of the catheter can be placed into a container of fluid, such as saline, during priming so that the fluid in the container, and not air, is aspirated through the tip of the catheter when the vacuum source is applied. In other embodiments, the tip of the catheter may be blocked (for example, using a plug) so that air is not aspirated from the tip of the catheter when the vacuum source is applied. In certain embodiments, the priming process may be automated such that a user can provide a single command and each catheter (and in some embodiments, each corresponding catheter hub) can be primed, sequentially (for example, as described with respect to FIGS. 20A-20C) or simultaneously.

Additional details regarding fluidics systems are disclosed in U.S. patent application Ser. No. 17/879,614, entitled Multi Catheter System With Integrated Fluidics Management, filed Aug. 2, 2022, which is hereby expressly incorporated in its entirety herein.

Fluid resistance within a lumen may be greater when there is a reduction in cross sectional luminal area for flow, for example, when a second interventional device (e.g., a catheter or guidewire) extends within the lumen of a first interventional device. The amount of fluid resistance can be affected by the length of the cross sectional narrowing, for example, due to a depth of axial insertion of the second interventional device within the first interventional device. A second interventional device extending partially through the lumen of a first interventional device will provide a smaller length of cross-sectional narrowing, and accordingly may result in a lower fluid resistance within the lumen of the first catheter, than if the second interventional device were to extend entirely through the lumen of the first interventional device. Thus, fluid resistance can be lowered by at least partially decreasing a depth of axial insertion (i.e., axial overlap) of a second interventional device into the lumen through which fluid is to be injected (e.g., a length of the second interventional device into its concentrically adjacent lumen).

In some embodiments, over certain depths of insertion of a second interventional device within a first interventional device (for example, when the second interventional device is at or near a maximum insertion depth within the first interventional device), the size of the fluid channel between the devices (e.g., the annular lumen between the first interventional device and the second interventional device) can lead to higher than desirable amounts of fluid resistance during a priming procedure. In some embodiments, the depth of insertion of the second interventional device within the first interventional device can be decreased to reduce the pressure needed to prime the catheter and reduce internal interference.

In some embodiments, a catheter in the interventional device assembly can be separated from the other interventional devices for priming to reduce the pressure needed to prime the catheter and reduce internal interference. The catheter being primed may be separated from the interventional devices within the lumen of the catheter by proximally retracting the interventional devices within the lumen of the catheter. For example, the interventional devices within the lumen of the catheter being primed can be proximally retracted from the catheter being primed as far as possible while still maintaining a nested or stacked relationship (e.g., at least about 2 cm or 5 cm or more axial overlap) in order to minimize the pressure needed to prime the catheter and minimize internal interference. In other words, a catheter can be separated from more proximal interventional devices for priming while a distal tip of an adjacent proximal interventional device is still positioned within the lumen of the catheter.

In some embodiments, the axial overlap may be between about 2 cm and about cm, between about 2 cm and 10 cm, between about 2 cm and 5 cm, between about 5 cm and cm, between about 5 cm and 10 cm, or any other suitable range. In some embodiments, the axial overlap may be at least about 2 cm, at least about 5 cm, at least about 10 cm, at least about 20 cm, no more than 2 cm, no more than 5 cm, no more than 10 cm, no more than 20 cm, about 2 cm, about 5 cm, about 10 cm, about 20 cm, or any other suitable amount.

In some embodiments, the robotic drive table can be programed to proximally retract the inner interventional device(s) from the catheter being primed as much as possible while still maintaining a nested or stacked relationship. In other embodiments, the robotic drive table can be programmed to separate inner devices from the catheter being primed to a distance sufficient to optimize the length of the unobstructed lumen and result in an amount of fluid resistance lower than a threshold value. After the catheter being primed is separated from the other interventional devices, the catheter can be primed by flushing the catheter with fluid, such as saline.

After the catheter is primed, it may be returned to an initial position and a next catheter of the interventional device assembly can be separated from the other interventional devices within its lumen for priming. This sequence can be repeated for each catheter of the interventional device assembly. While the foregoing describes separating catheters to be primed by retraction of inner interventional devices, an outer catheter may also be separated from inner interventional devices by distally axially advancing the outer catheter relative to the inner interventional devices. An example of a priming process is described with respect to FIGS. 20A-20C.

Figure 20A:
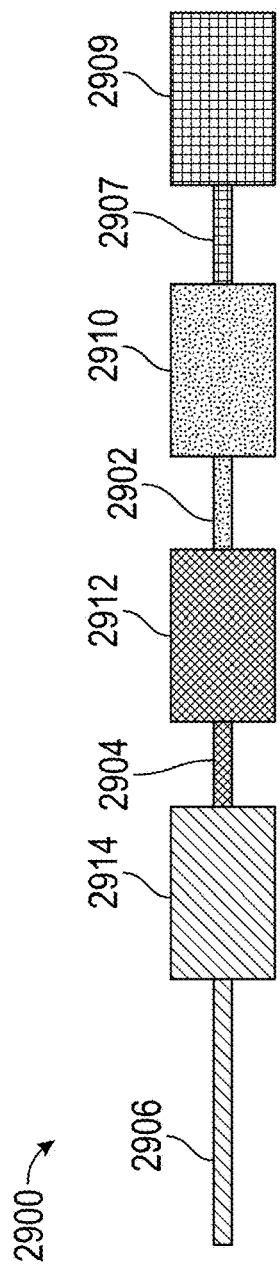
FIGS. 20A-20C depict an example sequence of steps of priming a catheter assembly in a stacked configuration.
Figure 20B:
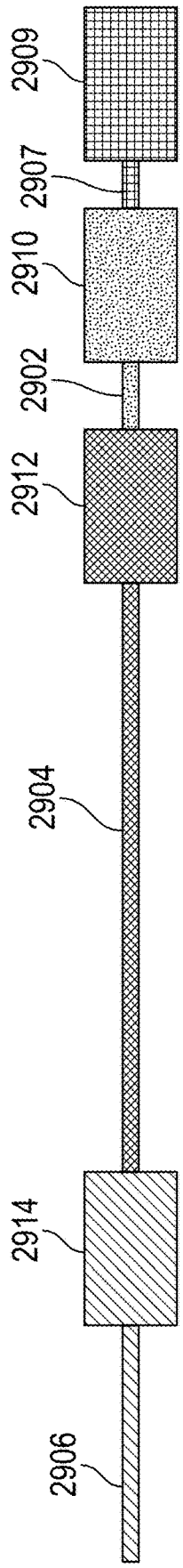

FIG. 20A depicts the interventional device assembly 2900 assembled in a concentric stack and axially compressed configuration. As shown in FIG. 20A, the interventional devices can be fully nested within each other. This may be the configuration following unpackaging of the device assembly 2900 and placement onto the robotic drive table. A priming sequence may begin by distally axially advancing the catheter 2906 and hub 2914 relative to the catheter 2904, hub 2912, catheter 2902, hub 2910, guidewire 2907, and hub 2909, for example, as far as possible while maintaining a distal tip of the catheter 2904 within the lumen of the catheter 2906, as shown in FIG. 20B, or to a distance that will result in a desirable amount of fluid resistance for priming. The catheter 2906 can then be primed by introducing priming fluid using the fluidics system. Priming the catheter 2906 can include priming the hub 2914. For example, in certain embodiments, the hub 2914 or a hemostasis valve coupled thereto can include fluidics connections to receive priming fluid from the fluidics system. After priming, the catheter 2906 can be returned to its initial position (e.g., the fully axially compressed configuration) as shown in FIG. 20A.

Figure 20C:
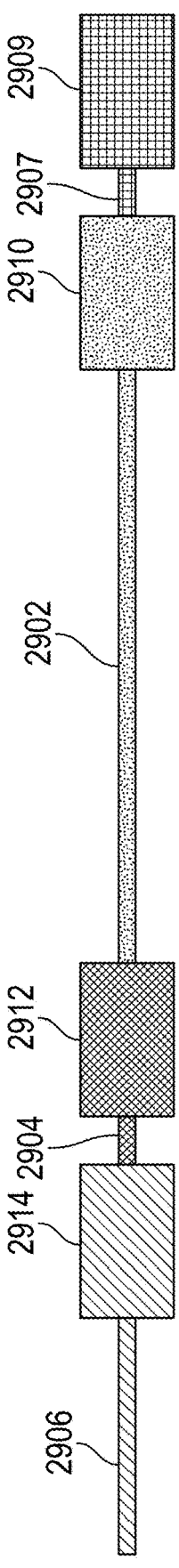

After the catheter 2906 is primed and returned to its initial position, the catheter 2904 and hub 2912 can be distally axially advanced relative to the catheter 2902, hub 2910, guidewire 2907 and hub 2909 (also distally axially advancing the catheter 2906 and hub 2914 without changing or minimally changing their relative position with respect to catheter 2904), for example, as far as possible while maintaining a distal tip of the catheter 2902 within the lumen of the catheter 2904, as shown in FIG. 20C, or to a distance that will result in a desirable amount of fluid resistance for priming. The catheter 2904 can then be primed by introducing priming fluid using the fluidics system. Priming the catheter 2904 can include priming the hub 2912. For example, in certain embodiments, the hub 2912 or a hemostasis valve coupled thereto can include fluidics connections to receive priming fluid from the fluidics system. After priming, the catheter 2904 and catheter 2906 can be returned to their initial positions (e.g., the fully axially compressed configuration) as shown in FIG. 20A.

After the catheter 2904 is primed and returned to its initial position, the catheter 2902 and hub 2910 can be distally axially advanced relative to the guidewire 2907 and hub 2909 (also distally axially advancing the catheter 2906, hub 2914, catheter 2904, and hub 2912 without changing or minimally changing their relative positions with respect to the catheter 2902), for example, as far as possible while maintaining a distal tip of the guidewire 2907 within the lumen of the catheter 2902, or to a distance that will result in a desirable amount of fluid resistance for priming. The catheter 2902 can then be primed by introducing priming fluid using the fluidics system. Priming the catheter 2902 can include priming the hub 2910. For example, in certain embodiments, the hub 2910 or a hemostasis valve coupled thereto can include fluidics connections to receive priming fluid from the fluidics system. After priming, the catheter 2902 and catheters 2904 and 2906 can be returned to their initial positions (e.g., the fully axially compressed configuration) shown in FIG. 20A.

In alternative embodiments, each of the catheters can be distally separated from one another simultaneously for priming. For example, the catheter 2902 can be distally separated from the guidewire 2907 while maintaining the distal tip of the guidewire 2907 in the lumen of the catheter 2902, the catheter 2904 can be distally separated from the catheter 2902 while maintaining the distal tip of the catheter 2902 in the lumen of the catheter 2904, and the catheter 2906 can be distally separated from the catheter 2904 while maintaining the distal tip of the catheter 2904 in the lumen of the catheter 2906 simultaneously. However, an embodiment in which only one set of adjacent hubs is separated at a time, as described with respect to FIGS. 20A-20C, can provide a smaller overall length of the assembly at any particular time, which can allow for use with a smaller robotic drive system. While separation of outer catheters from their inner interventional devices is described as distally axially advancing the catheters relative to their inner interventional devices, separation can include proximally retracting the inner interventional devices from the outer catheters.

As described above, in some embodiments, the catheters 2902, 2904, and 2906 may be assembled into the concentric stack orientation illustrated in FIG. 17 prior to flushing the catheters to remove air by displacing it with a fluid such as saline. This is preferably accomplished in each fluid lumen, such as, for example, the annular lumen between the catheter 2906 and the catheter 2904 and in between each of the additional concentric interventional devices in the concentric stack. Infusing saline under pressure may displace substantially all of the air but some small bubbles may remain, adhering to the inside wall of an outer catheter (e.g., the guide catheter 2906), the outside wall of an inner catheter (e.g., the procedure catheter 2904), or both.

While saline is being introduced under pressure into the proximal end of the annular lumen (e.g., into a hub of the outer catheter or a hemostasis valve coupled thereto), the inner catheter may be moved with respect to the outer catheter, to disrupt the holding forces between the microbubbles and adjacent wall and allow the bubbles to be carried downstream and out through the distal opening of the lumen or removed via aspiration. The catheters may be moved axially, rotationally or both with respect to each other. In certain embodiments, the catheters may be reciprocated axially, rotationally, or both with respect to each other. In some embodiments, the catheters may be moved intermittently axially, rotationally, or both. In other embodiments, the catheters may be rotated continuously or in a constant direction.

In some implementations, a first catheter is moved reciprocally with respect to an adjacent catheter or guidewire such as axially over a stroke length in a range of from about 1 mm to about 250 mm, from about 10 mm to about 250 mm, from about 5 mm to about 125 mm, from about 25 mm to about 125 mm, from about 10 mm to about 50 mm, from about 15 mm to about 30 mm, from about 5 mm to about 30 mm, from about 15 mm to about 25 mm, from about 20 mm to about 40 mm, or any other suitable range. In some implementations, a first catheter is moved reciprocally with respect to an adjacent catheter or guidewire such as axially over a stroke length of at least 5 mm, at least 10 mm, at least 15 mm, at least 20 mm, at least 25 mm, at least 30 mm, at least 50 mm, no more than 10 mm, no more than 20 mm, no more than 25 mm, no more than 30 mm, no more than 50 mm, no more than 125 mm, no more than 150 mm, about 5 mm, about 10 mm, about 15 mm, about 20 mm, about 25 mm, about 30 mm, about 50 mm, or any other suitable stroke length.

In some implementations, a first catheter is moved reciprocally with respect to an adjacent catheter or guidewire such as axially at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as axially at a reciprocation frequency of at least 0.5 Hz, at least 1 Hz, at least 2 Hz, at least 5 Hz, at least Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In one implementation, a first catheter is moved reciprocally with respect to the adjacent catheter or guidewire such as axially over a stroke length in a range of from about 0.5 inches to about 10 inches, or from about one inch to about 5 inches at a reciprocation frequency of no more than about 5 cycles per second or two cycles per second or less.

In some implementations, a first catheter is moved reciprocally with respect to an adjacent catheter or guidewire such as rotationally over an angle of rotation per stroke in a range of from about 5 degrees to about 180 degrees, from about 5 degrees to about 360 degrees, from about 15 degrees to about 180 degrees, from about 15 degrees to about 150 degrees, from about 15 degrees to about 120 degrees, from about 15 degrees to about 90 degrees, form about degrees to about 60 degrees, from about 15 degrees to about 30 degrees, from about 30 degrees to about 180 degrees, from about 30 degrees to about 150 degrees, from about 30 degrees to about 120 degrees, from about 30 degrees to about 90 degrees, form about 30 degrees to about 60 degrees, from about 60 degrees to about 180 degrees, from about 60 degrees to about 150 degrees, from about 60 degrees to about 120 degrees, from about 60 degrees to about 90 degrees, from about 90 degrees to about 180 degrees, from about 90 degrees to about 150 degrees, from about 90 degrees to about 120 degrees, from about 120 degrees to about 180 degrees, from about 120 degrees to about 150 degrees, from about 150 degrees to about 180 degrees or any other suitable range. In some implementations, a first catheter is moved reciprocally with respect to an adjacent catheter or guidewire such as rotationally over an angle of rotation per stroke of at least 5 degrees, at least 15 degrees, at least 30 degrees, at least 60 degrees, at least 90 degrees, at least 120 degrees, at least 150 degrees, at least 180 degrees, at least 360 degrees, no more than 5 degrees, no more than 15 degrees, no more than 30 degrees, no more than 60 degrees, no more than 90 degrees, no more than 120 degrees, no more than 150 degrees, no more than 180 degrees, no more than 360 degrees, about 5 degrees, about 15 degrees, about 30 degrees, about 60 degrees, about 90 degrees, about 120 degrees, about 150 degrees, about 180 degrees, about 360 degrees, or any other suitable angle.

In some implementations, a first catheter is moved reciprocally with respect to an adjacent catheter or guidewire such as rotationally at a reciprocation frequency in a range of from about 0.5 Hz to about 1 Hz, from about 1 Hz to about 5 Hz, from about 1 Hz to about Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as rotationally at a reciprocation frequency of at least 0.5 Hz, at least 1 Hz, at least 2 Hz, at least Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In some implementations, a first catheter is moved reciprocally with respect to an adjacent catheter or guidewire for a number of reciprocations between 1 and 200, between 1 and 100, between 1 and 50, between 1 and 25, between 1 and 15, between 1 and 10, between 1 and 5, between 5 and 25, between 5 and 15, between 5 and 10, or any other suitable range. In some implementations, a first catheter is moved reciprocally with respect to an adjacent catheter or guidewire for at least 1 reciprocation, at least 2 reciprocations, at least 5 reciprocations, at least 10 reciprocations, at least 15 reciprocations, at least 25 reciprocations, at least 50 reciprocations, no more than 5 reciprocations, no more than 10 reciprocations, no more than 15 reciprocations, no more than 25 reciprocations, no more 50 than reciprocations, no more than 100 reciprocations, no more than 200 reciprocations, about 1 reciprocation, about 2 reciprocations, about 5 reciprocations, about 10 reciprocations, about 25 reciprocations, about 50 reciprocations, about 100 reciprocations, about 200 reciprocations, or any other suitable number. One reciprocation can include a movement (axially or rotationally) from a first position to a second position followed by a return from the second position to the first position.

In some implementations, a first catheter is moved reciprocally with respect to an adjacent catheter or guidewire over a length of time in a range of from 1 about second to about 60 seconds, from about 1 second to about 45 seconds, from about 1 second to about 30 seconds, from about 1 second to about 20 seconds, from about 1 second to about 15 seconds, from about 1 second to about 10 seconds, from about 5 seconds to about 45 seconds, from about 5 seconds to about 30 seconds, from about 5 seconds to about 20 seconds, from about 5 seconds to about 15 seconds, from about 5 seconds to about 10 seconds, from about 10 seconds to about 30 seconds, form about 10 seconds to about 20 seconds, or any other suitable range. In some implementations, a first catheter is moved reciprocally with respect to an adjacent catheter or guidewire over a length of time of at least 1 second, at least 5 seconds, at least 10 seconds, at least 15 seconds, at least 20 seconds, at least 30 seconds, at least 45 seconds, at least 60 seconds, no more than 5 seconds, no more than 10 seconds, no more than 15 seconds, no more than 20 seconds, no more than 30 seconds, no more than 45 seconds, no more than 60 seconds, about 5 seconds, about 10 seconds, about 15 seconds, about 20 seconds, about 30 seconds, about 45 seconds, about 60 seconds, or any other suitable length of time.

Reciprocation of adjacent catheters to disrupt microbubbles may be accomplished manually by grasping the corresponding catheter hubs and manually moving the catheters axially or rotationally with respect to each other while delivering pressurized saline. Alternatively, such as in a robotically driven system, a processor may be configured to robotically drive at least one of two adjacent catheter hubs (for example, at least one of hub 2914 and hub 2912) to achieve relative movement between the adjacent catheters thereby disrupting and expelling microbubbles, such as in response to user activation of a flush control.

The reciprocation of adjacent catheters may generate shear forces that dislodge the air bubbles. In some embodiments, the shear force can be increased by increasing the flow rate of the solution (e.g., saline) being provided by the fluidics system. In certain embodiments, both flow rate and relative movement between adjacent catheters are controlled to dislodge air bubbles.

In some embodiments, after each catheter is primed by the fluidics system, an ultrasound bubble detector may be used to confirm that the catheters are substantially free of air bubbles. For example, an ultrasound chip (such as mounted within a hub adjacent a catheter receiving lumen) may be run along the length of the catheters to confirm that no air bubbles remain in the system.

An example of a priming process including reciprocal movement of adjacent catheters is described with respect to FIGS. 21A-21B.

FIG. 21A depicts the interventional device assembly 2900 assembled in a concentric stack configuration. As shown in FIG. 21A, the interventional devices can be fully nested within each other. This may be the configuration following unpackaging of the device assembly 2900 and placement onto the robotic drive table. Alternatively, individual interventional devices of the device assembly 2900 can be assembled into the device assembly 2900 on the drive table.

A priming sequence may begin by priming the catheter 2906. In some embodiments, the catheter 2906 can be primed by introducing saline under pressure into the lumen of the catheter 2906 while generating reciprocal movement of catheter 2906 and/or hub 2914, axially, rotationally or both, relative to the catheter 2904. Priming the catheter 2906 can include priming the hub 2914. For example, in certain embodiments, the hub 2914 or a hemostasis valve coupled thereto can include fluidics connections to receive priming fluid from the fluidics system. In certain embodiments, the catheter 2906 and/or hub 2914 can be axially agitated back and forth along a longitudinal axis of the catheter 2906 (e.g., between the position of FIG. 21A and the position of FIG. 21B). Axial and/or rotational reciprocal motion of the catheter 2906 and/or hub 2914 can be performed manually or by a robotic drive table.

In some embodiments, priming of the catheter 2906 may be performed by introducing saline under pressure into the lumen of the catheter 2906 while generating reciprocal movement of the catheter 2904 and/or hub 2912, axially, rotationally or both, relative to the catheter 2906. Axial and/or rotational reciprocal motion of the catheter 2904 and/or hub 2912 can be performed manually or by a robotic drive table.

In some embodiments, priming of the catheter 2906 may be performed by introducing saline under pressure into the lumen of the catheter 2906 while generating reciprocal movement of both the catheter 2906 (and/or hub 2914) and the catheter 2904 (and/or hub 2912), axially, rotationally or both, relative to one another.

In some embodiments, after priming the catheter 2906, the catheter 2906 can be returned to an initial position as shown in FIG. 21A.

In some embodiments, after the catheter 2906 is primed, the catheter 2904 can be primed. Priming the catheter 2904 can include priming the hub 2912. For example, in certain embodiments, the hub 2912 or a hemostasis valve coupled thereto can include fluidics connections to receive priming fluid from the fluidics system. In some embodiments, the catheter 2904 can be primed by introducing saline under pressure into the lumen of the catheter 2904 while generating reciprocal movement of the catheter 2904 and/or hub 2912, axially, rotationally or both, relative to the catheter 2902.

In some embodiments, priming of the catheter 2904 may be performed by introducing saline under pressure into the lumen of the catheter 2904 while generating reciprocal movement of the catheter 2902 and/or hub 2910, axially, rotationally or both, relative to the catheter 2904. Axial and/or rotational reciprocal motion of the catheter 2902 and/or hub 2910 can be performed manually or by a robotic drive table.

In some embodiments, priming of the catheter 2904 may be performed by introducing saline under pressure into the lumen of the catheter 2904 while generating reciprocal movement of both the catheter 2904 (and/or hub 2912) and the catheter 2902 (and/or hub 2910), axially, rotationally or both, relative to one another.

In some embodiments, after priming the catheter 2904, the catheter 2904 can be returned to an initial position as shown in FIG. 21A.

In some embodiments, after the catheter 2904 is primed, the catheter 2902 can be primed. Priming the catheter 2902 can include priming the hub 2910. For example, in certain embodiments, the hub 2910 or a hemostasis valve coupled thereto can include fluidics connections to receive priming fluid from the fluidics system. In some embodiments, the catheter 2902 can be primed by introducing saline under pressure into the lumen of the catheter 2902 while generating reciprocal movement of the catheter 2902 and/or hub 2910, axially, rotationally or both, relative to the guidewire 2907.

In some embodiments, priming of the catheter 2902 may be performed by introducing saline under pressure into the lumen of the catheter 2902 while generating reciprocal movement of the guidewire 2907 and/or hub 2909, axially, rotationally or both, relative to the catheter 2902. Axial and/or rotational reciprocal motion of the guidewire 2907 and/or hub 2909 can be performed manually or by a robotic drive table.

In some embodiments, priming of the catheter 2902 may be performed by introducing saline under pressure into the lumen of the catheter 2902 while generating reciprocal movement of both the catheter 2902 (and/or hub 2910) and the guidewire 2907 (and/or hub 2909), axially, rotationally or both, relative to one another.

In some embodiments, after priming the catheter 2902, the catheter 2902 can be returned to an initial position as shown in FIG. 21A.

In the priming sequence described herein with respect to FIGS. 21A and 21B, the catheters are primed in order starting with the catheter 2906, followed by the catheter 2904, and then followed by the catheter 2902. However, it is contemplated that the catheters may be primed in any order. The catheters may be primed in series as described above with respect to FIGS. 21A and 21B. Alternatively, two or more of the catheters or each of the catheters may be primed in parallel.

In certain embodiments, priming the catheters can include decreasing a depth of axial insertion (i.e., axial overlap) of a second interventional device into the lumen of a first interventional device through which fluid is to be injected (e.g., a length of the second interventional device into its concentrically adjacent lumen), as described with respect. to FIGS. 20A-20C, and also generating relative reciprocal movement, axially, rotationally or both, between first interventional device and the second interventional device during priming, as discussed with respect to FIGS. 21A and 21B.

EXAMPLES

Additional embodiments are disclosed in further detail in the following examples, which are not in any way intended to limit the scope of the claims.

Figure 22:
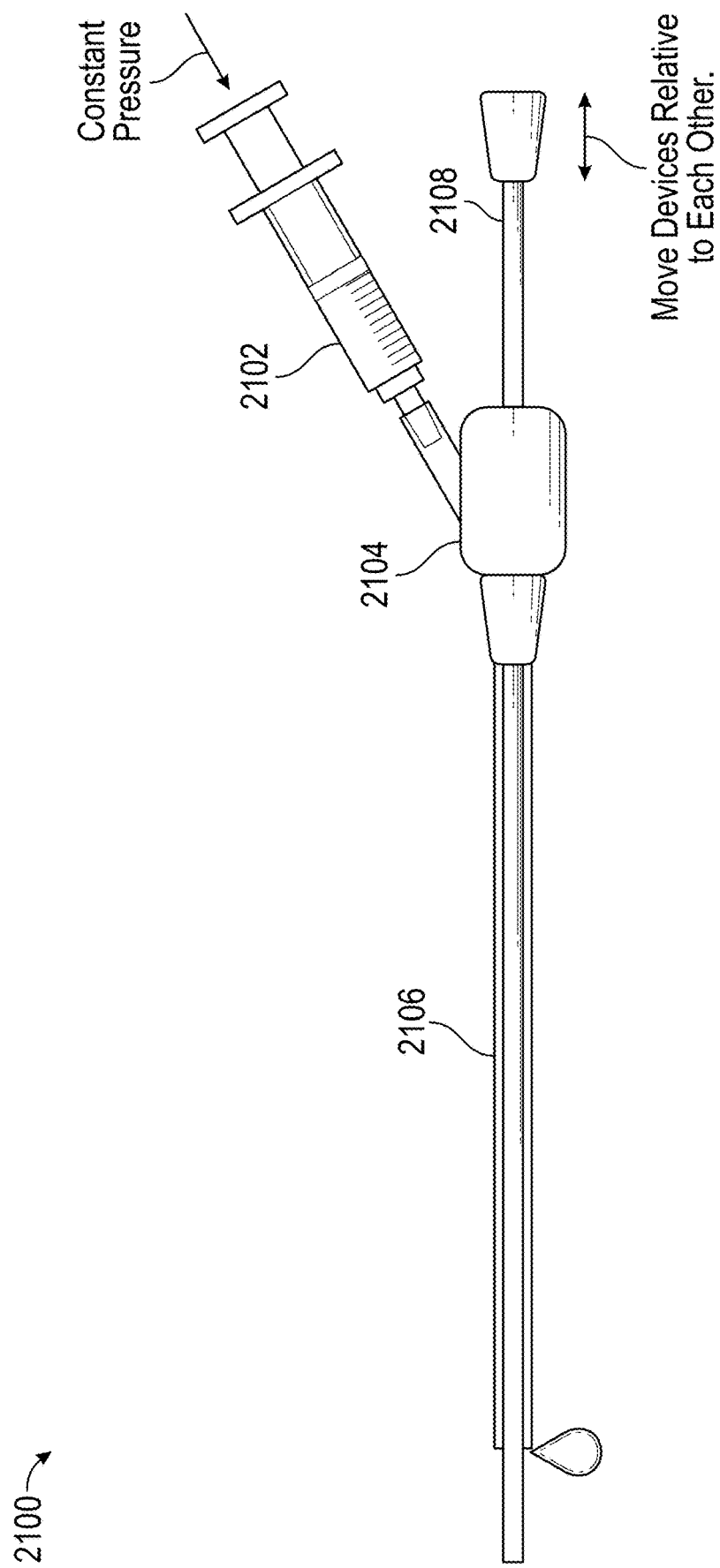
FIG. 22 depicts an example test system for the priming process depicted in FIGS. 21A-21B.
Figure 23A:
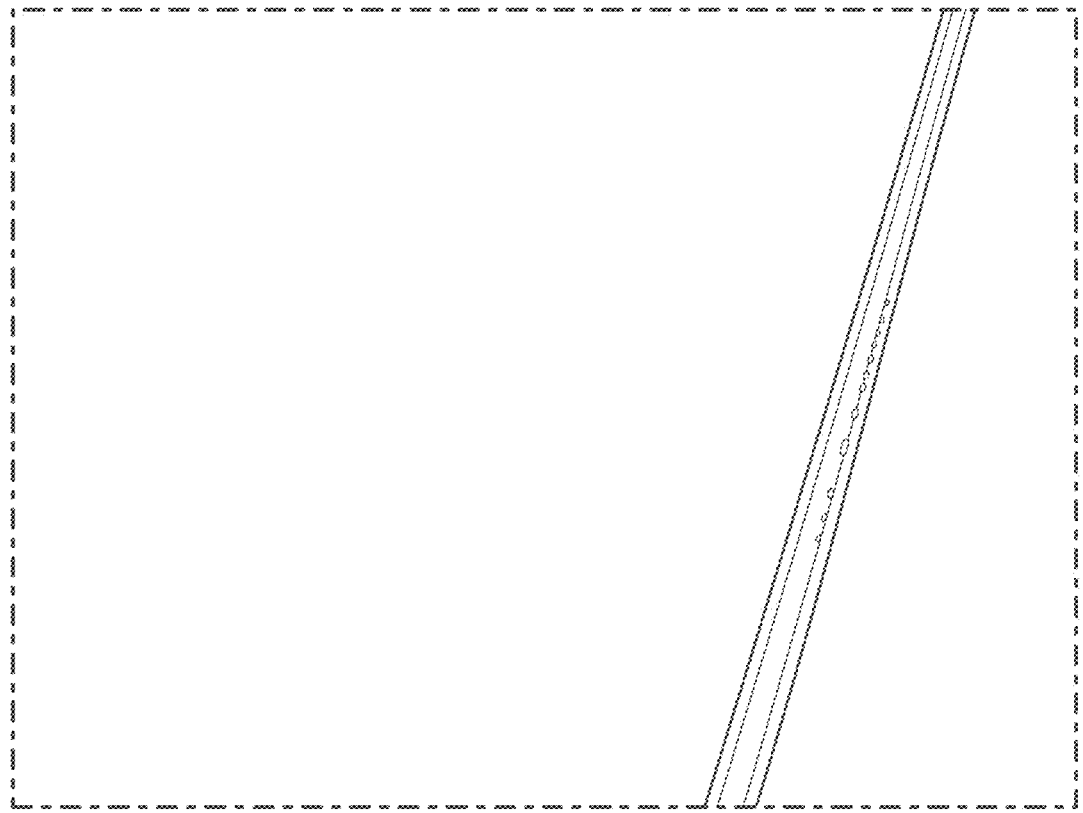
FIG. 23A depicts an example of a catheter assembly.

FIG. 22 is a diagram of a test system that was used for detecting the removal of air bubbles between concentrically stacked catheters. The test system included an inner catheter 2108 positioned within an interior lumen of an outer catheter 2106 in a concentric stack. The outer catheter 2106 was coupled to a rotating hemostasis valve 2104. The hemostasis valve 2104 was coupled to a syringe 2102 so that fluid injected using the syringe would flow through the lumen between the inner catheter 2108 and the outer catheter 2016. In the test system, the inner catheter 2108 had a diameter of about 0.071 inches. The outer catheter 2106 had a diameter of about 0.088 inches. The outer catheter 2106 was transparent to permit visualization of bubbles within the lumen. A distal end of the outer catheter 2108 allowed for small volumes of fluid to exit the outer catheter. FIG. 23A is a photograph showing the catheter 2106 and catheter 2108 in a concentric stack, prior to injection of fluid.

Example 1

Figure 23B:
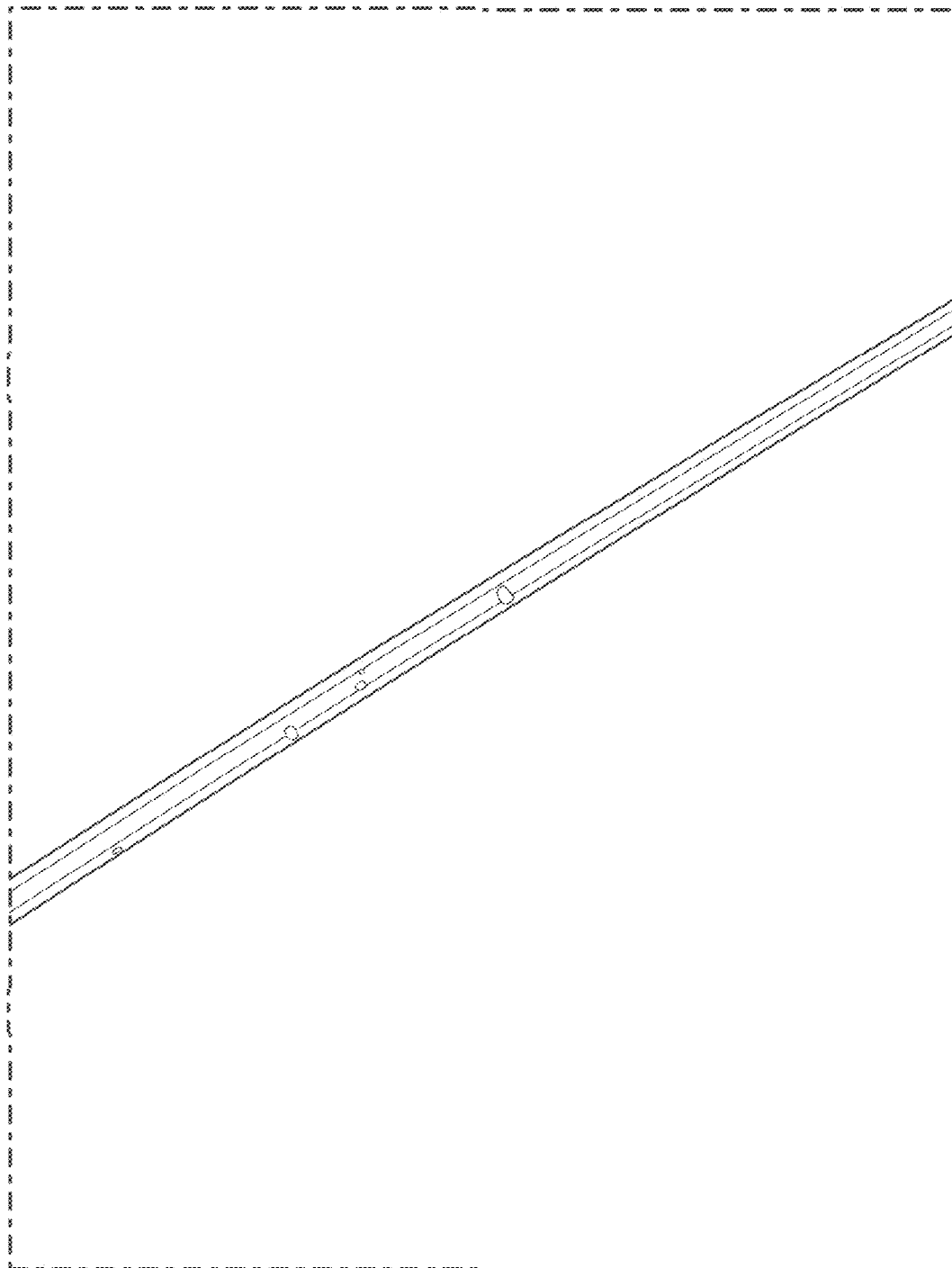
FIG. 23B depicts an example of a catheter assembly after a priming procedure.

In a first example, the syringe 2102 was used to inject water at a constant pressure of about 150 psi through the hemostasis valve 2104 without moving the catheter 2106 or the catheter 2108. FIG. 23B is a photograph showing the catheter 2106 and catheter 2108 following the injection of water. As shown in FIG. 23B, bubbles are present within the lumen between the catheter 2106 and the catheter 2108.

Example 2

Figure 23C:
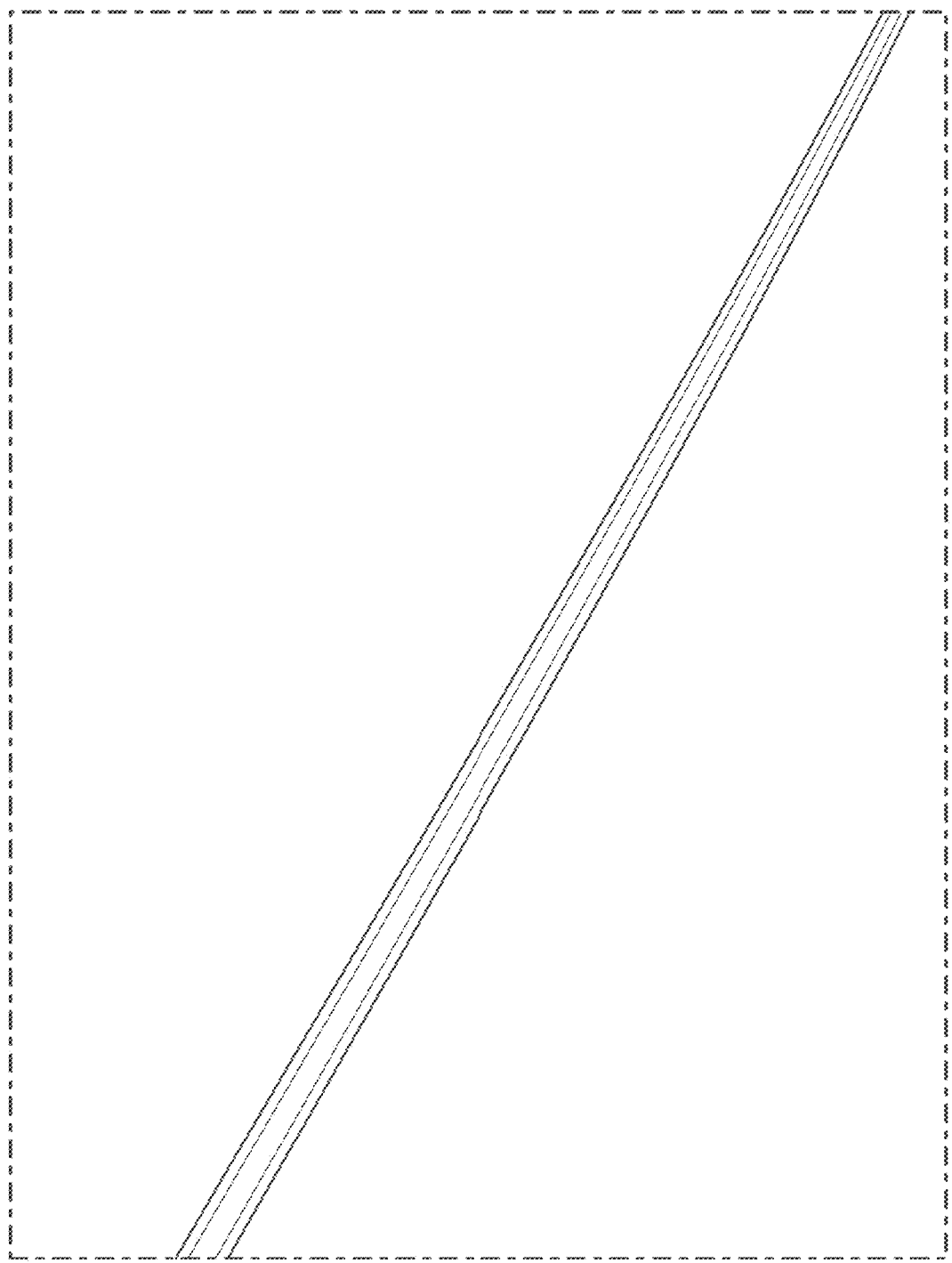
FIG. 23C depicts an example of a catheter assembly after a priming procedure including relative movement between adjacent catheters.

In a second example, the syringe 2102 was used to inject water at a constant pressure of about 150 psi through the hemostasis valve 2104. Shortly after beginning to inject water, axial reciprocal movement of the inner catheter 2108 was performed for about 10 seconds. The reciprocal movement was performed at a frequency of about 1 Hz (or less) and a stroke length of about 20 mm (or more). FIG. 23C is a photograph showing the catheter 2106 and the catheter 2108 following the axial reciprocal movement. As shown in FIG. 23C, the lumen between the catheter 2106 and the catheter 2108 was substantially free of bubbles.

Example 3

In a third example, an outer catheter having a diameter of about 0.071 inches and an inner catheter having a diameter of about 0.035 inches were used in the test system 2100 instead of the outer catheter 2106 and the inner catheter 2108 described with respect to Examples 1 and 2. A syringe 2102 was used to inject water at a constant pressure of about 150 psi through a hemostasis valve 2104 coupled to the outer catheter. Shortly after beginning to inject water, axial reciprocal movement of the inner catheter was performed for about 10 seconds. The reciprocal movement was performed at a frequency of about 1 Hz (or less) and a stroke length of about 20 mm (or more). Following the axial reciprocal movement, the lumen between the outer and inner catheters was found to be substantially free of bubbles by visual inspection.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

The foregoing represents one specific implementation of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

Various systems and methods are described herein primarily in the context of a neurovascular access or procedure (e.g., neurothrombectomy). However, the catheters, systems (e.g., drive systems), and methods disclosed herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

What is claimed is:

1. A drive system for achieving supra-aortic access and neurovascular treatment site access, comprising:
    a guidewire hub configured to adjust an axial position and a rotational position of a guidewire;
    a procedure catheter hub configured to adjust an axial position of a procedure catheter;
    a guide catheter hub configured to adjust an axial position of a guide catheter; and
    an access catheter hub configured to adjust an axial position and a rotational position of an access catheter;
    wherein:
        the guidewire hub is configured to couple to a guidewire hub adapter by magnetically coupling the guidewire hub to a first drive magnet;
        the access catheter hub is configured to couple to an access catheter hub adapter by magnetically coupling the access catheter hub to a second drive magnet;
        the guide catheter hub is configured to couple to a guide catheter hub adapter by magnetically coupling the guide catheter hub to a third drive magnet; and
        the procedure catheter hub is configured to couple to a procedure catheter hub adapter by magnetically coupling the procedure catheter hub to a fourth drive magnet, wherein the first drive magnet, the second drive magnet, the third drive magnet, and the fourth drive magnet are independently movably carried by a drive table.

2. The drive system of claim 1, wherein the procedure catheter hub is further configured to laterally deflect a distal deflection zone of the procedure catheter.

3. The drive system of claim 1, further comprising a first driven magnet on the guidewire hub configured to cooperate with the first drive magnet such that the first driven magnet moves in response to movement of the first drive magnet.

4. The drive system of claim 3, wherein the first drive magnet is configured to move outside of a sterile field while separated from the first driven magnet by a sterile field barrier while the first driven magnet is within the sterile field.

5. The drive system of claim 4, further comprising a second driven magnet on the access catheter hub configured to cooperate with the second drive magnet such that the second driven magnet is configured to move in response to movement of the second drive magnet, wherein the second drive magnet is configured to move outside of the sterile field while separated from the second driven magnet by the barrier while the second driven magnet is within the sterile field.

6. The drive system of claim 5, further comprising a third driven magnet on the guide catheter hub configured to cooperate with the third drive magnet such that the third driven magnet is configured to move in response to movement of the third drive magnet, wherein the third drive magnet is configured to move outside of the sterile field while separated from the third driven magnet by the barrier while the third driven magnet is within the sterile field.

7. The drive system of claim 6, further comprising a fourth driven magnet on the procedure catheter hub configured to cooperate with the fourth drive magnet such that the fourth driven magnet is configured to move in response to movement of the fourth drive magnet, wherein the fourth drive magnet is configured to move outside of the sterile field while separated from the fourth driven magnet by the barrier while the fourth driven magnet is within the sterile field.

8. The drive system of claim 3, wherein a position of the first drive magnet is movable in response to manipulation of a procedure drive control on a control console in electrical communication with the drive table.

9. The drive system of claim 1, wherein the procedure catheter is an aspiration catheter.

10. The drive system of claim 1, wherein the procedure catheter is an embolic deployment catheter.

11. The drive system of claim 1, wherein the procedure catheter is a stent deployment catheter.

12. The drive system of claim 1, wherein the procedure catheter is a flow diverter deployment catheter.

13. The drive system of claim 1, wherein the procedure catheter is a diagnostic angiographic catheter.

14. The drive system of claim 1, wherein the procedure catheter is a stent retriever catheter.

15. The drive system of claim 1, wherein the procedure catheter is a balloon catheter.

16. The drive system of claim 1, wherein the procedure catheter is a catheter to facilitate percutaneous valve repair or replacement.

17. The drive system of claim 1, wherein the procedure catheter is an ablation catheter.

18. A method of achieving supra-aortic access and neurovascular treatment site access, comprising the steps of:
    providing a drive system comprising:
        a guidewire hub configured to adjust an axial position and a rotational position of a guidewire;

a procedure catheter hub configured to adjust an axial position of a procedure catheter;

a guide catheter hub configured to adjust an axial position of a guide catheter; and an access catheter hub configured to adjust an axial position and a rotational position of an access catheter; and moving at least one of the guidewire hub, the procedure catheter hub, the guide catheter hub, and the access catheter hub to drive movement of at least one of the guidewire, the procedure catheter, the guide catheter, and the access catheter;

wherein:
the guidewire hub is configured to couple to a guidewire hub adapter by magnetically coupling the guidewire hub to a first drive magnet;

the access catheter hub is configured to couple to an access catheter hub adapter by magnetically coupling the access catheter hub to a second drive magnet;

the guide catheter hub is configured to couple to a guide catheter hub adapter by magnetically coupling the guide catheter hub to a third drive magnet; and the procedure catheter hub is configured to couple to a procedure catheter hub adapter by magnetically coupling the procedure catheter hub to a fourth drive magnet, wherein the first drive magnet, the second drive magnet, the third drive magnet, and the fourth drive magnet are independently movably carried by a drive table.

19. The method of claim 18, further comprising controlling the procedure catheter hub to laterally deflect a distal deflection zone of the procedure catheter.

20. The method of claim 18, wherein the drive system comprises:

a first driven magnet on the guidewire hub configured to cooperate with the first drive magnet such that the first driven magnet moves in response to movement of the first drive magnet, wherein the first drive magnet is configured to move outside of a sterile field while separated from the first driven magnet by a sterile field barrier while the first driven magnet is within the sterile field;

a second driven magnet on the access catheter hub configured to cooperate with the second drive magnet such that the second driven magnet is configured to move in response to movement of the second drive magnet, wherein the second drive magnet is configured to move outside of the sterile field while separated from the second driven magnet by the barrier while the second driven magnet is within the sterile field;

a third driven magnet on the guide catheter hub configured to cooperate with the third drive magnet such that the third driven magnet is configured to move in response to movement of the third drive magnet, wherein the third drive magnet is configured to move outside of the sterile field while separated from the third driven magnet by the barrier while the third driven magnet is within the sterile field; and a fourth driven magnet on the procedure catheter hub configured to cooperate with the fourth drive magnet such that the fourth driven magnet is configured to move in response to movement of the fourth drive magnet, wherein the fourth drive magnet is configured to move outside of the sterile field while separated from the fourth driven magnet by the barrier while the fourth driven magnet is within the sterile field.

* * * * *